US010189887B2

(12) United States Patent
Legembre et al.

(10) Patent No.: US 10,189,887 B2
(45) Date of Patent: Jan. 29, 2019

(54) POLYPEPTIDES AND USES THEREOF FOR REDUCING CD95-MEDIATED CELL MOTILITY

(71) Applicants: INSERM (INSTITUT NATIONAL DE LA SANTÉ ET DE LA RECHERCHE MÉDICALE), Paris (FR); UNIVERSITÉ DE BORDEAUX, Bordeaux (FR); UNIVERSITÉ DE RENNES, Rennes (FR); ECOLE DES HAUTES ETUDES EN SANTÉ PUBLIQUE (EHESP), Rennes (FR); UNIVERSITÉ DES ANTILLES ET DE LA GUYANE, Pointe-à-Pitre (FR); INSTITUT BERGONIÉ, Bordeaux (FR); UNIVERSITY OF NOTTINGHAM, Nottingham (GB)

(72) Inventors: Patrick Legembre, Rennes (FR); Pierre Vacher, Bordeaux (FR); Doriane Sanseau, Rennes (FR); Aubin Penna, Rennes (FR); Robin Flynn, Sutton Bonington Leicestershire (GB)

(73) Assignees: INSERM (INSTITUT NATIONAL DE LA SANTE ET DE LA RECHERCHE MEDICALE), Paris (FR); UNIVERSITE DE BORDEAUX, Bourdeaux (FR); UNIVERSITE DE RENNES, Rennes (FR); ECOLE DES HAUTES ETUDES EN SANTE PUBLIQUE (EHESP), Rennes (FR); UNIVERSITE DES ANTILLES ET DE LA GUYANE, Pointe-a-Pitre (FR); INSTITUTE BERGONIE, Bordeaux (FR); UNIVERSITY OF NOTTINGHAM, Nottingham (FR)

( * ) Notice: Subject to any disclaimer, the term of this patent is extended or adjusted under 35 U.S.C. 154(b) by 0 days.

(21) Appl. No.: 15/304,550

(22) PCT Filed: Apr. 16, 2015

(86) PCT No.: PCT/EP2015/058245
§ 371 (c)(1),
(2) Date: Oct. 17, 2016

(87) PCT Pub. No.: WO2015/158810
PCT Pub. Date: Oct. 22, 2015

(65) Prior Publication Data
US 2017/0044234 A1 Feb. 16, 2017

(30) Foreign Application Priority Data
Apr. 17, 2014 (EP) .................... 14305570

(51) Int. Cl.
C07K 14/70 (2006.01)
C07K 16/00 (2006.01)
C07K 14/705 (2006.01)
C07K 14/525 (2006.01)
G01N 33/68 (2006.01)
A61K 38/00 (2006.01)

(52) U.S. Cl.
CPC ...... *C07K 14/70575* (2013.01); *C07K 14/525* (2013.01); *C07K 16/00* (2013.01); *G01N 33/6872* (2013.01); *A61K 38/00* (2013.01); *C07K 2319/74* (2013.01); *G01N 2333/70575* (2013.01); *G01N 2333/70578* (2013.01); *G01N 2500/02* (2013.01)

(58) Field of Classification Search
CPC .................. C07K 14/70575; C07K 16/00
See application file for complete search history.

(56) References Cited

U.S. PATENT DOCUMENTS

| 6,015,938 | A * | 1/2000 | Boyle | ........... C07K 14/70578 800/14 |
| 6,653,113 | B1 | 11/2003 | Dean | |
| 6,846,637 | B1 * | 1/2005 | Chiodi | ........... C07K 14/4747 424/130.1 |
| 7,288,519 | B2 * | 10/2007 | Greene | ........... C07K 14/70578 514/18.9 |
| 2011/0245146 | A1 * | 10/2011 | Payne | ........... C07K 14/47 514/1.2 |

FOREIGN PATENT DOCUMENTS

| EP | 2322927 A1 | 5/2011 |
| WO | 2004/085478 A2 | 10/2004 |
| WO | 2009/014702 A2 | 1/2009 |
| WO | 2010/003766 A2 | 1/2010 |
| WO | 2014/060848 A2 | 4/2014 |

OTHER PUBLICATIONS

Khafagy et al., 2012, Oral biodrug delivery using cell-penetrating peptide, Advanced Drug Delivery Reviews, 64: 531-539.*

* cited by examiner

*Primary Examiner* — Amber D Steele
(74) *Attorney, Agent, or Firm* — W&C IP

(57) ABSTRACT

The present invention relates to polypeptides and uses thereof for reducing CD95-meditated cell motility. In particular, the present invention relates to a polypeptide having an amino acid sequence having at least 70% of identity with the amino acid sequence ranging from the amino-acid residue at position 175 to the amino-acid residue at position 191 in SEQ ID NO:1.

Figure 1:
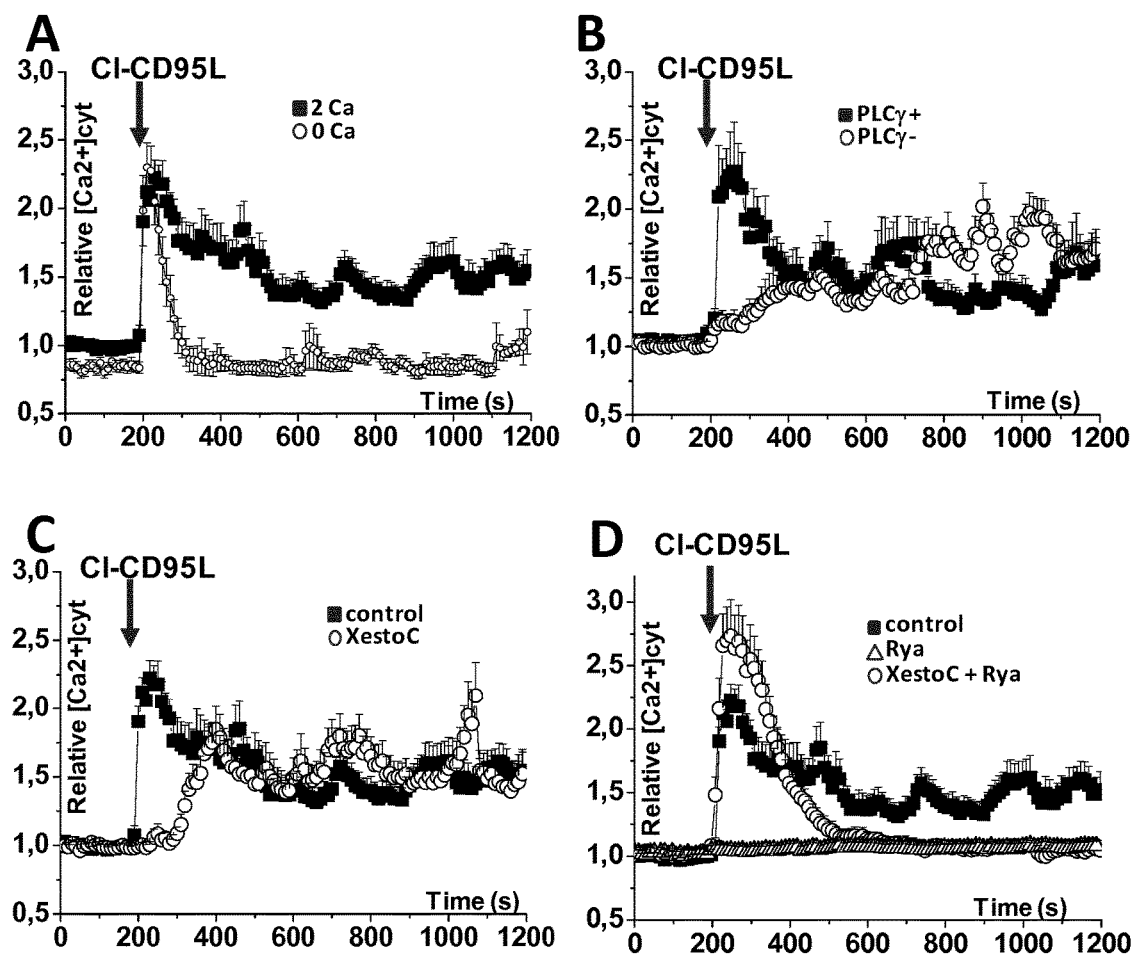

11 Claims, 15 Drawing Sheets
Specification includes a Sequence Listing.

POLYPEPTIDES AND USES THEREOF FOR REDUCING CD95-MEDIATED CELL MOTILITY

FIELD OF THE PRESENT INVENTION

The present invention relates to polypeptides and uses thereof for reducing CD95-meditated cell motility.

BACKGROUND OF THE PRESENT INVENTION

CD95 ligand (CD95L, also known as FasL) belongs to the TNF (Tumor Necrosis Factor) family and is the ligand for the "death receptor" CD95 (Fas/APO1). CD95L is a transmembrane "cytokine" whose extracellular domain can be cleaved by metalloproteases, to produce a soluble ligand. This soluble form was initially described as an inert ligand that competes with its membrane-bound counterpart for binding to CD95, thus acting as an antagonist of the death signal. More recent findings have shown that metalloprotease-cleaved-CD95L (cl-CD95L) can actively participate in aggravating inflammation in chronic inflammatory disorders, such as systemic lupus erythematosus (and may exert pro-oncogenic functions by promoting the survival of ovarian and liver cancers and chemotherapy resistance of lung cancers). Binding of transmembrane CD95L to CD95 leads to the recruitment of the adaptor protein Fas-associated death domain protein (FADD) to the intracellular region of CD95 called the death domain (DD). In turn, FADD binds to caspases 8 and 10. This CD95/FADD/caspase complex is known as the Death-Inducing Signaling Complex (DISC) and plays a pivotal role in the initiation of the apoptotic signal. By contrast, cl-CD95L fails to induce DISC formation and instead promotes the formation of an atypical receptosome that we have designated Motility-Inducing Signaling Complex (MISC) (Tauzin S, Chaigne-Delalande B, Selva E, Khadra N, Daburon S, Contin-Bordes C, et al. The naturally processed CD95L elicits a c-yes/calcium/ PI3K-driven cell migration pathway. PLoS Biol. 2011; 9:e1001090.). Accordingly, a compound able to reduce the reducing CD95-meditated cell motility is highly desirable.

SUMMARY OF THE PRESENT INVENTION

The present invention relates to polypeptides and uses thereof for reducing CD95-meditated cell motility.

DETAILED DESCRIPTION OF THE PRESENT INVENTION

The death receptor CD95 plays a pivotal role in immune surveillance. Binding of CD95L to CD95 leads to the formation of a molecular complex consisting in the adaptor protein FADD and the proteases caspase-8 and -10. This complex is named death inducing signaling complex (DISC). We found that CD95 engagement activates the phospholipase Cγ1 (PLCγ1), which in turn evokes a calcium response through activation of Ins3P Ins1,4,5 trisphosphate (IP3) receptor (IP3R) and then multimerization of the plasma membrane calcium channel Orai1. Tumor cells exposed to CD95L undergo a redistribution of Orai1 into the CD95 aggregate where it triggers a localized calcium influx transiently inhibiting the DISC formation via the recruitment of Protein kinase C β2 (PKCβ2). Also, this calcium signal is able to promote cell motility. Overall, the inventors' data clearly indicate that inhibition of the CD95-mediated $Ca^{2+}$ response turns out to be an attractive process to simultaneously sensitize tumor cells to death and impair their motility. More recently, the inventors found that while PLCγ1 activation impairs DISC formation, FADD and caspase-8 do not participate in the $Ca^{2+}$ signal suggesting that the formation of a different molecular complex is required to evoke the calcium response in cells exposed to CD95L. Pursuing this analysis, they also identified the intracellular domain of CD95 responsible for PLCγ1 activation and its blockade by a TAT-conjugated peptide inhibits the CD95-mediated calcium signal. In summary, disrupting the CD95-mediated $Ca^{2+}$ response by using this peptide represents a new therapeutic mechanism to reduce the CD95-mediated cell motility and thus offers means for the treatment of cancers but also auto-immune diseases.

Accordingly an object of the present invention relates to a polypeptide having an amino acid sequence having at least 70% of identity with the amino acid sequence ranging from the amino-acid residue at position 175 to the amino-acid residue at position 191 in SEQ ID NO: 1.

As used herein, the polypeptide which ranges from the amino acid residue at position 175 to the amino acid residue at position 191 is named "CID 175-191".

As used herein, the term "CD95" has its general meaning in the art and refers to CD95 to the receptor present on the surface of mammalian cells, which has been originally shown to have the capacity to induce apoptosis upon binding of the trimeric form of its cognate ligand, CD95L (Krammer, P. H. (2000). CD95's deadly mission in the immune system. Nature 407, 789-795). CD95 is also known as FasR or Apo-1. An exemplary amino acid sequence of CD95 is shown as SEQ ID NO:1.

SEQ ID NO: 1:
>sp|P25445|TNR6_HUMAN without signal peptide:
RLSSKSVNAQVTDINSKGLELRKTVTTVETQNLEGLHHDGQFCHKPCPPG

ERKARDCTVNGDEPDCVPCQEGKEYTDKAHFSSKCRRCRLCDEGHGLEVE

INCTRTQNTKCRCKPNFFCNSTVCEHCDPCTKCEHGIIKECTLTSNTKCK

EEGSRSNLGWLCLLLLPIPLIVWVKRKEVQKTCRKHRKENQGSHESPTLN

PETVAINLSDVDLSKYITTIAGVMTLSQVKGFVRKNGVNEAKIDEIKNDN

VQDTAEQKVQLLRNWHQLHGKKEAYDTLIKDLKKANLCTLAEKIQTIILK

DITSDSENSNFRNEIQSLV

According to the invention a first amino acid sequence having at least 70% of identity with a second amino acid sequence means that the first sequence has 70; 71; 72; 73; 74; 75; 76; 77; 78; 79; 80; 81; 82; 83; 84; 85; 86; 87; 88; 89; 90; 91; 92; 93; 94; 95; 96; 97; 98; or 99% of identity with the second amino acid sequence. Amino acid sequence identity is typically determined using a suitable sequence alignment algorithm and default parameters, such as BLAST P (Karlin and Altschul, 1990).

In particular the polypeptide of the present invention is a functional conservative variant of the polypeptide for which the amino acid sequence ranges from the amino acid residue at position 175 to the amino acid residue at position 191. As used herein the term "function-conservative variant" are those in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Accordingly, a "function-conservative variant" also includes a polypeptide which has at least 70% amino acid identity and which has the same or substantially similar properties or functions as the native or parent protein to which it is compared (i.e. inhibition of the CD95-mediated cell motility). Functional properties of the polypeptide of the present invention could typically be assessed in any functional assay as described in the EXAMPLES 1&2.

In some embodiments, the polypeptide of the present invention has an amino acid sequence having at least 70% of identity with the amino acid sequence ranging from the amino-acid residue at position 175 to the amino-acid residue at position 192 in SEQ ID NO:1.

In some embodiments, the polypeptide of the present invention has an amino acid sequence having at least 70% of identity with the amino acid sequence ranging from the amino-acid residue at position 175 to the amino-acid residue at position 193 in SEQ ID NO:1.

In some embodiments, the polypeptide of the present invention has an amino acid sequence having at least 70% of identity with the amino acid sequence ranging from the amino-acid residue at position 175 to the amino-acid residue at position 194 in SEQ ID NO:1.

In some embodiments, the polypeptide of the present invention has an amino acid sequence having at least 70% of identity with the amino acid sequence ranging from the amino-acid residue at position 175 to the amino-acid residue at position 195 in SEQ ID NO:1.

In some embodiments, the polypeptide of the present invention has an amino acid sequence having at least 70% of identity with the amino acid sequence ranging from the amino-acid residue at position 175 to the amino-acid residue at position 196 in SEQ ID NO:1.

In some embodiments, the polypeptide of the present invention has an amino acid sequence having at least 70% of identity with the amino acid sequence ranging from the amino-acid residue at position 175 to the amino-acid residue at position 196 in SEQ ID NO:1.

In some embodiments, the polypeptide of the present invention has an amino acid sequence having at least 70% of identity with the amino acid sequence ranging from the amino-acid residue at position 175 to the amino-acid residue at position 197 in SEQ ID NO:1.

In some embodiments, the polypeptide of the present invention has an amino acid sequence having at least 70% of identity with the amino acid sequence ranging from the amino-acid residue at position 175 to the amino-acid residue at position 198 in SEQ ID NO:1.

In some embodiments, the polypeptide of the present invention has an amino acid sequence having at least 70% of identity with the amino acid sequence ranging from the amino-acid residue at position 175 to the amino-acid residue at position 199 in SEQ ID NO:1.

In some embodiments, the polypeptide of the present invention has an amino acid sequence having at least 70% of identity with the amino acid sequence ranging from the amino-acid residue at position 175 to the amino-acid residue at position 200 in SEQ ID NO:1.

In some embodiments, the polypeptide of the present invention has an amino acid sequence having at least 70% of identity with the amino acid sequence ranging from the amino-acid residue at position 175 to the amino-acid residue at position 201 in SEQ ID NO:1.

In some embodiments, the polypeptide of the present invention has an amino acid sequence having at least 70% of identity with the amino acid sequence ranging from the amino-acid residue at position 175 to the amino-acid residue at position 202 in SEQ ID NO:1.

In some embodiments, the polypeptide of the present invention has an amino acid sequence having at least 70% of identity with the amino acid sequence ranging from the amino-acid residue at position 175 to the amino-acid residue at position 203 in SEQ ID NO:1.

In some embodiments, the polypeptide of the present invention has an amino acid sequence having at least 70% of identity with the amino acid sequence ranging from the amino-acid residue at position 175 to the amino-acid residue at position 204 in SEQ ID NO:1.

In some embodiments, the polypeptide of the present invention has an amino acid sequence having at least 70% of identity with the amino acid sequence ranging from the amino-acid residue at position 175 to the amino-acid residue at position 205 in SEQ ID NO:1.

In some embodiments, the polypeptide of the present invention has an amino acid sequence having at least 70% of identity with the amino acid sequence ranging from the amino-acid residue at position 175 to the amino-acid residue at position 206 in SEQ ID NO:1.

In some embodiments, the polypeptide of the present invention has an amino acid sequence having at least 70% of identity with the amino acid sequence ranging from the amino-acid residue at position 175 to the amino-acid residue at position 207 in SEQ ID NO:1.

In some embodiments, the polypeptide of the present invention has an amino acid sequence having at least 70% of identity with the amino acid sequence ranging from the amino-acid residue at position 175 to the amino-acid residue at position 208 in SEQ ID NO:1.

In some embodiments, the polypeptide of the present invention has an amino acid sequence having at least 70% of identity with the amino acid sequence ranging from the amino-acid residue at position 175 to the amino-acid residue at position 209 in SEQ ID NO:1.

In some embodiments, the polypeptide of the present invention has an amino acid sequence having at least 70% of identity with the amino acid sequence ranging from the amino-acid residue at position 175 to the amino-acid residue at position 210 in SEQ ID NO:1.

As used herein, the polypeptide which ranges from the amino acid residue at position 175 to the amino acid residue at position 210 is named "Calcium-inducing domain" or "CID".

In some embodiments, the polypeptide of the present invention comprises 18; 19; 20; 21; 22; 23; 24; 25; 26; 27; 28; 29; 30; 31; 32; 33; 34; 35; 36; 37; 38; 39; 40; 41; 42; 43; 44; 45; 46; 47; 48; 49; 50; 51; 52; 53; 54; 55; 56; 57; 58; 59; 60; 61; 62; 63; 64; 65; 66; 67; 68; 69; 70; 71; 72; 73; 74; 75; 76; 77; 78; 79; 80; 81; 82; 83; 84; 85; 86; 87; 88; 89; 90; 91; 92; 93; 94; 95; 96; 97; 98; 99; or 100 amino acids. In some embodiments, the polypeptide of the present invention comprises less than 50 amino acids. In some embodiments, the polypeptide of the present invention comprises less than 30 amino acids. In some embodiments, the polypeptide of the present invention comprises less than 25 amino acids. In some embodiments, the polypeptide of the present invention comprises less than 20 amino acids.

In some embodiments, the polypeptide of the present invention is stapled. A "stapled" peptide is a peptide comprising a selected number of standard or nonstandard amino acids, further comprising at least two moieties capable of undergoing reaction to promote carbon-carbon bond formation, that has been contacted with a reagent to generate at least one cross-linker between the at least two moieties, which modulates, for example, peptide stability. More particularly "peptide stapling" is a term coined for a synthetic methodology used to covalently join two olefin-containing side chains present in a polypeptide chain using an olefin metathesis reaction (J. Org. Chem. (2001) 66(16); Blackwell et al., Angew. Chem. Int. Ed. (1998) 37:3281). Stapling of a peptide using a hydrocarbon cross-linker created from an olefin metathesis reaction has been shown to help maintain a peptide's native conformation, particularly under physiological conditions (U.S. Pat. Nos. 7,192,713; 7,723,469; 7,786,072; U.S. Patent Application Publication Nos: 2010-0184645; 2010-0168388; 2010-0081611; 2009-0176964; 2009-0149630; 2006-0008848; PCT Application Publication Nos: WO 2010/011313; WO 2008/121767; WO 2008/095063; WO 2008/061192; WO2005/044839; Schafmeister et al., J. Am. Chem. Soc. (2000) 122:5891-5892; Walensky et al., Science (2004) 305: 1466-1470; each of which is incorporated herein by reference in their entirety). The stapled peptide strategy in which an all-hydrocarbon cross-link is generated by olefin metathesis is an efficient approach to increase the helical character of peptides to target a-helical binding motifs. Unlike their unstapled analogues these hydrocarbon-stapled peptides have shown to be a-helical, protease-resistant, and cell permeable.

In some embodiments, the polypeptide of the present invention is fused to at least one heterologous polypeptide (i.e. a polypeptide which is not derived to CD95) to create a fusion protein. The term "fusion protein" refers to the polypeptide according to the invention that is fused directly or via a spacer to at least one heterologous polypeptide. In some embodiments, the fusion protein comprises the polypeptide according to the invention that is fused either directly or via a spacer at its C-terminal end to the N-terminal end of the heterologous polypeptide, or at its N-terminal end to the C-terminal end of the heterologous polypeptide.

As used herein, the term "directly" means that the (first or last) amino acid at the terminal end (N or C-terminal end) of the polypeptide is fused to the (first or last) amino acid at the terminal end (N or C-terminal end) of the heterologous polypeptide. In other words, in this embodiment, the last amino acid of the C-terminal end of said polypeptide is directly linked by a covalent bond to the first amino acid of the N-terminal end of said heterologous polypeptide, or the first amino acid of the N-terminal end of said polypeptide is directly linked by a covalent bond to the last amino acid of the C-terminal end of said heterologous polypeptide.

As used herein, the term "spacer" refers to a sequence of at least one amino acid that links the polypeptide of the present invention to the heterologous polypeptide. Such a spacer may be useful to prevent steric hindrances.

In some embodiments, the heterologous polypeptide is a cell-penetrating peptide, a Transactivator of Transcription (TAT) cell penetrating sequence, a cell permeable peptide or a membranous penetrating sequence. The term "cell-penetrating peptides" are well known in the art and refers to cell permeable sequence or membranous penetrating sequence such as penetratin, TAT mitochondrial penetrating sequence and compounds (Bechara and Sagan, 2013; Jones and Sayers, 2012; Khafagy el and Morishita, 2012; Malhi and Murthy, 2012). In a particular embodiment, the heterologous polypeptide is an internalization sequence derived either from the homeodomain of Drosophila Antennapedia/Penetratin (Antp) protein (amino acids 43-58; SEQ ID NO:2) or the Transactivator of Transcription (TAT) cell penetrating sequences (SEQ ID NO:3).

SEQ ID NO: 2 for *Drosophila Antennapedia/Penetratin (Antp)* (amino acids 43-58):
RQIKIWFQNRRMKWKK SEQ ID NO: 3 for Tat cell penetrating sequence Tat (47-57)
YGRKKRRQRRR The polypeptides or fusion proteins of the present invention may be produced by any technique known per se in the art, such as, without limitation, any chemical, biological, genetic or enzymatic technique, either alone or in combination. For instance, knowing the amino acid sequence of the desired sequence, one skilled in the art can readily produce said polypeptides or fusion proteins, by standard techniques for production of amino acid sequences. For instance, they can be synthesized using well-known solid phase method, typically using a commercially available peptide synthesis apparatus (such as that made by Applied Biosystems, Foster City, Calif.) and following the manufacturer's instructions. Alternatively, the polypeptides or fusion proteins of the present invention can be synthesized by recombinant DNA techniques as is now well-known in the art. For example, these fragments can be obtained as DNA expression products after incorporation of DNA sequences encoding the desired (poly)peptide into expression vectors and introduction of such vectors into suitable eukaryotic or prokaryotic hosts that will express the desired polypeptide, from which they can be later isolated using well-known techniques. Polypeptides or fusion proteins of the present invention can be used in an isolated (e.g., purified) form or contained in a vector, such as a membrane or lipid vesicle (e.g. a liposome).

In some embodiments, it is contemplated that polypeptides or fusion proteins according to the invention may be modified in order to improve their therapeutic efficacy. Such modification of therapeutic compounds may be used to decrease toxicity, increase circulatory time, or modify biodistribution. For example, the toxicity of potentially important therapeutic compounds can be decreased significantly by combination with a variety of drug carrier vehicles that modify biodistribution. For instance, a strategy for improving drug viability is the utilization of water-soluble polymers. Various water-soluble polymers have been shown to modify biodistribution, improve the mode of cellular uptake, change the permeability through physiological barriers; and modify the rate of clearance from the body. To achieve either a targeting or sustained-release effect, water-soluble polymers have been synthesized that contain drug moieties as terminal groups, as part of the backbone, or as pendent groups on the polymer chain. For example, Pegylation is a well-established and validated approach for the modification of a range of polypeptides (Chapman, 2002). The benefits include among others: (a) markedly improved circulating half-lives in vivo due to either evasion of renal clearance as a result of the polymer increasing the apparent size of the molecule to above the glomerular filtration limit, and/or through evasion of cellular clearance mechanisms; (b) reduced antigenicity and immunogenicity of the molecule to which PEG is attached; (c) improved pharmacokinetics; (d) enhanced proteolytic resistance of the conjugated protein (Cunningham-Rundles et. al., 1992); and (e) improved thermal and mechanical stability of the PEGylated polypeptide. Therefore, in some embodiments, the polypeptides of the present invention may be covalently linked with one or more polyethylene glycol (PEG) group(s).

A further object of the present invention relates to a nucleic acid sequence encoding for a polypeptide or a fusion protein according to the invention.

As used herein, a sequence "encoding" an expression product, such as a RNA, polypeptide, protein, or enzyme, is a nucleotide sequence that, when expressed, results in the production of that RNA, polypeptide, protein, or enzyme, i.e., the nucleotide sequence encodes an amino acid sequence for that polypeptide, protein or enzyme. A coding sequence for a protein may include a start codon (usually ATG) and a stop codon.

These nucleic acid sequences can be obtained by conventional methods well known to those skilled in the art. Typically, said nucleic acid is a DNA or RNA molecule, which may be included in a suitable vector, such as a plasmid, cosmid, episome, artificial chromosome, phage or viral vector.

So, a further object of the present invention relates to a vector and an expression cassette in which a nucleic acid molecule encoding for a polypeptide or a fusion protein of the present invention is associated with suitable elements for controlling transcription (in particular promoter, enhancer and, optionally, terminator) and, optionally translation, and also the recombinant vectors into which a nucleic acid molecule in accordance with the invention is inserted. These recombinant vectors may, for example, be cloning vectors, or expression vectors.

As used herein, the terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence. Any expression vector for animal cell can be used. Examples of suitable vectors include pAGE107 (Miyaji et al., 1990), pAGE103 (Mizukami and Itoh, 1987), pHSG274 (Brady et al., 1984), pKCR (O'Hare et al., 1981), pSG1 beta d2-4 (Miyaji et al., 1990) and the like. Other examples of plasmids include replicating plasmids comprising an origin of replication, or integrative plasmids, such as for instance pUC, pcDNA, pBR, and the like. Other examples of viral vectors include adenoviral, retroviral, herpes virus and AAV vectors. Such recombinant viruses may be produced by techniques known in the art, such as by transfecting packaging cells or by transient transfection with helper plasmids or viruses. Typical examples of virus packaging cells include PA317 cells, PsiCRIP cells, GPenv+ cells, 293 cells, etc. Detailed protocols for producing such replication-defective recombinant viruses may be found for instance in WO 95/14785, WO 96/22378, U.S. Pat. Nos. 5,882,877, 6,013,516, 4,861,719, 5,278,056 and WO 94/19478. Examples of promoters and enhancers used in the expression vector for animal cell include early promoter and enhancer of SV40 (Mizukami and Itoh, 1987), LTR promoter and enhancer of Moloney mouse leukemia virus (Kuwana et al., 1987), promoter (Mason et al., 1985) and enhancer (Gillies et al., 1983) of immunoglobulin H chain and the like.

A further aspect of the present invention relates to a host cell comprising a nucleic acid molecule encoding for a polypeptide or a fusion protein according to the invention or a vector according to the invention. In particular, a subject of the present invention is a prokaryotic or eukaryotic host cell genetically transformed with at least one nucleic acid molecule or vector according to the invention.

The term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. A host cell that receives and expresses introduced DNA or RNA has been "transformed".

In a particular embodiment, for expressing and producing polypeptides or fusion proteins of the present invention, prokaryotic cells, in particular *E. coli* cells, will be chosen. Actually, according to the invention, it is not mandatory to produce the polypeptide or the fusion protein of the present invention in a eukaryotic context that will favour post-translational modifications (e.g. glycosylation). Furthermore, prokaryotic cells have the advantages to produce protein in large amounts. If a eukaryotic context is needed, yeasts (e.g. *saccharomyces* strains) may be particularly suitable since they allow production of large amounts of proteins. Otherwise, typical eukaryotic cell lines such as CHO, BHK-21, COS-7, C127, PER.C6, YB2/0 or HEK293 could be used, for their ability to process to the right post-translational modifications of the fusion protein of the present invention.

The construction of expression vectors in accordance with the invention, and the transformation of the host cells can be carried out using conventional molecular biology techniques. The polypeptide or the fusion protein of the present invention, can, for example, be obtained by culturing genetically transformed cells in accordance with the invention and recovering the polypeptide or the fusion protein expressed by said cell, from the culture. They may then, if necessary, be purified by conventional procedures, known in themselves to those skilled in the art, for example by fractional precipitation, in particular ammonium sulfate precipitation, electrophoresis, gel filtration, affinity chromatography, etc. In particular, conventional methods for preparing and purifying recombinant proteins may be used for producing the proteins in accordance with the invention.

A further aspect of the present invention relates to a method for producing a polypeptide or a fusion protein of the present invention comprising the step consisting of: (i) culturing a transformed host cell according to the invention under conditions suitable to allow expression of said polypeptide or fusion protein; and (ii) recovering the expressed polypeptide or fusion protein.

The polypeptides and fusion proteins of the present invention are particularly suitable of reducing CD95-mediated cell motility and thus may find various therapeutic applications.

In some embodiments, the polypeptide or fusion protein of the present invention is particularly suitable for reducing CD95-mediated cancer cell motility. In some embodiments, the polypeptides and fusion proteins of the present invention are particularly suitable for the treatment of cancer in a subject in need thereof. As used herein, the term "cancer" has its general meaning in the art and includes, but is not limited to, solid tumors and blood borne tumors. The term cancer includes diseases of the skin, tissues, organs, bone, cartilage, blood and vessels. The term "cancer" further encompasses both primary and metastatic cancers. Examples of cancers that may be treated by methods and compositions of the present invention include, but are not limited to, cancer cells from the bladder, blood, bone, bone marrow, brain, breast, colon, esophagus, gastrointestine, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma;

basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous; adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; and roblastoma, malignant; Sertoli cell carcinoma; leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxo sarcoma; liposarcoma; leiomyo sarcoma; rhabdomyo sarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangio sarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; Hodgkin's lymphoma; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

In some embodiments, the polypeptide or fusion protein of the present is particularly suitable for the treatment of triple negative breast cancer. As used herein the expression "Triple negative breast cancer" has its general meaning in the art and means that said breast cancer lacks receptors for the hormones estrogen (ER-negative) and progesterone (PR-negative), and for the protein HER2.

In some embodiments, the polypeptide or fusion protein of the present invention is particularly suitable for the prevention of metastases (e.g. in a subject suffering from a triple negative breast cancer).

In some embodiments, the present invention relates to the polypeptide or the fusion protein of the present invention for use in enhancing therapeutic efficacy of cancer treatment in a subject in need thereof. In some embodiments, the polypeptide or the fusion protein of the present invention may be administered sequentially or concomitantly with one or more therapeutic active agent such as chemotherapeutic or radiotherapeutic agents. Examples of chemotherapeutics include but are not limited to fludarabine, gemcitabine, capecitabine, methotrexate, mercaptopurine, thioguanine, hydroxyurea, cytarabine, cyclophosphamide, ifosfamide, nitrosoureas, platinum complexes such as cisplatin, carboplatin and oxaliplatin, mitomycin, dacarbazine, procarbazine, epipodophyllotoxins such as etoposide and teniposide, camptothecins such as irinotecan and topotecan, bleomycin, doxorubicin, idarubicin, daunorubicin, dactinomycin, plicamycin, mitoxantrone, L-asparaginase, doxorubicin, epirubicin, 5-fluorouracil and 5-fluorouracil combined with leucovorin, taxanes such as docetaxel and paclitaxel, levamisole, estramustine, nitrogen mustards, nitrosoureas such as carmustine and lomustine, vinca alkaloids such as vinblastine, vincristine, vindesine and vinorelbine, imatinib mesylate, hexamethylmelamine, kinase inhibitors, phosphatase inhibitors, ATPase inhibitors, tyrphostins, protease inhibitors, inhibitors herbimycin A, genistein, erbstatin, and lavendustin A. In some embodiments, additional therapeutic active agents may be selected from, but are not limited to, one or a combination of the following class of agents: alkylating agents, plant alkaloids, DNA topoisomerase inhibitors, anti-folates, pyrimidine analogs, purine analogs, DNA antimetabolites, taxanes, podophyllotoxins, hormonal therapies, retinoids, photosensitizers or photodynamic therapies, angiogenesis inhibitors, antimitotic agents, isoprenylation inhibitors, cell cycle inhibitors, actinomycin, bleomycin, anthracyclines, MDR inhibitors and $Ca^{2+}$ ATPase inhibitors. The term "radiotherapeutic agent" as used herein, is intended to refer to any radiotherapeutic agent known to one of skill in the art to be effective to treat or ameliorate cancer, without limitation. For instance, the radiotherapeutic agent can be an agent such as those administered in brachytherapy or radionuclide therapy. Such methods can optionally further comprise the administration of one or more additional cancer therapies, such as, but not limited to, chemotherapies, and/or another radiotherapy.

In some embodiments, the polypeptide or fusion protein of the present invention is particularly suitable for reducing CD95-mediated lymphocyte (e.g. T cell) motility. In some embodiments, the polypeptide or fusion protein of the present invention is particularly suitable for the treatment of an auto-immune disease. As used herein, an "autoimmune disease" is a disease or disorder arising from and directed to an individual's own tissues. Examples of autoimmune diseases include, but are not limited to Addison's Disease, Allergy, Alopecia Areata, Alzheimer's disease, Antineutrophil cytoplasmic antibodies (ANCA)-associated vasculitis, Ankylosing Spondylitis, Antiphospho lipid Syndrome (Hughes Syndrome), arthritis, Asthma, Atherosclerosis, Atherosclerotic plaque, autoimmune disease (e.g., lupus, RA, MS, Graves' disease, etc.), Autoimmune Hemolytic Anemia, Autoimmune Hepatitis, Autoimmune inner ear disease, Autoimmune Lymphoproliferative syndrome, Autoimmune Myocarditis, Autoimmune Oophoritis, Autoimmune Orchitis, Azoospermia, Behcet's Disease, Berger's Disease, Bullous Pemphigoid, Cardiomyopathy, Cardiovascular disease, Celiac Sprue/Coeliac disease, Chronic Fatigue Immune Dysfunction Syndrome (CFIDS), Chronic idiopathic polyneuritis, Chronic Inflammatory Demyelinating, Polyradicalneuropathy (CIPD), Chronic relapsing polyneuropathy (Guillain-Barr syndrome), Churg-Strauss Syndrome (CSS), Cicatricial Pemphigoid, Cold Agglutinin Disease (CAD), chronic obstructive pulmonary disease (COPD), CREST syndrome, Crohn's disease, Dermatitis, Herpetiformis, Dermatomyositis, diabetes, Discoid Lupus, Eczema, Epidermolysis bullosa acquisita, Essential Mixed Cryoglobulinemia, Evan's Syndrome, Exopthalmos, Fibromyalgia, Goodpasture's Syndrome, Hashimoto's Thyroiditis, Idiopathic Pulmonary Fibrosis, Idiopathic Thrombocytopenia Purpura (ITP), IgA Nephropathy, immunoproliferative disease or disorder (e.g., psoriasis), Inflammatory bowel disease (IBD), including Crohn's disease and ulcerative colitis, Insulin Dependent Diabetes Mellitus (IDDM), Interstitial lung disease, juvenile diabetes, Juvenile Arthritis, juvenile idiopathic arthritis (JIA), Kawasaki's Disease, Lambert-Eaton Myasthenic Syndrome, Lichen Planus, lupus, Lupus Nephritis, Lymphoscytic Lypophisitis, Meniere's Disease, Miller Fish Syndrome/acute disseminated encephalomyeloradiculopathy, Mixed Connective Tissue Disease, Multiple Sclerosis (MS), muscular rheumatism, Myalgic encephalomyelitis (ME), Myasthenia Gravis, Ocular Inflammation, Pemphigus Foliaceus, Pemphigus Vulgaris, Pernicious Anaemia, Polyarteritis Nodosa, Polychondritis, Polyglandular Syndromes (Whitaker's syndrome), Polymyalgia Rheumatica, Polymyositis, Primary Agammaglobulinemia, Primary Biliary Cirrhosis/Autoimmune cholangiopathy, Psoriasis, Psoriatic arthritis, Raynaud's Phenomenon, Reiter's Syndrome/Reactive arthritis, Restenosis, Rheumatic Fever, rheumatic disease, Rheumatoid Arthritis, Sarcoidosis, Schmidt's syndrome, Scleroderma, Sjörgen's Syndrome, Stiff-Man Syndrome, Systemic Lupus Erythematosus (SLE), systemic scleroderma, Takayasu Arteritis, Temporal Arteritis/Giant Cell Arteritis, Thyroiditis, Type 1 diabetes, Type 2 diabetes, Ulcerative colitis, Uveitis, Vasculitis, Vitiligo, and Wegener's Granulomatosis.

In some embodiments, the polypeptide or fusion protein of the present invention is particularly suitable for the treatment of systemic lupus erythematosus.

In some embodiments, the polypeptide or fusion protein of the present invention is particularly suitable for the treatment of an inflammatory condition. The term "inflammatory condition" as used herein refers to acute or chronic localized or systemic responses to harmful stimuli, such as pathogens, damaged cells, physical injury or irritants, that are mediated in part by the activity of cytokines, chemokines, or inflammatory cells (e.g., neutrophils, monocytes, lymphocytes, macrophages) and is characterized in most instances by pain, redness, swelling, and impairment of tissue function. The inflammatory condition may be selected from the group consisting of: sepsis, septicemia, pneumonia, septic shock, systemic inflammatory response syndrome (SIRS), Acute Respiratory Distress Syndrome (ARDS), acute lung injury, aspiration pneumanitis, infection, pancreatitis, bacteremia, peritonitis, abdominal abscess, inflammation due to trauma, inflammation due to surgery, chronic inflammatory disease, ischemia, ischemia-reperfusion injury of an organ or tissue, tissue damage due to disease, tissue damage due to chemotherapy or radiotherapy, and reactions to ingested, inhaled, infused, injected, or delivered substances, glomerulonephritis, bowel infection, opportunistic infections, and for subjects undergoing major surgery or dialysis, subjects who are immunocompromised, subjects on immunosuppressive agents, subjects with HIV/AIDS, subjects with suspected endocarditis, subjects with fever, subjects with fever of unknown origin, subjects with cystic fibrosis, subjects with diabetes mellitus, subjects with chronic renal failure, subjects with bronchiectasis, subjects with chronic obstructive lung disease, chronic bronchitis, emphysema, or asthma, subjects with febrile neutropenia, subjects with meningitis, subjects with septic arthritis, subjects with urinary tract infection, subjects with necrotizing fasciitis, subjects with other suspected Group A *streptococcus* infection, subjects who have had a splenectomy, subjects with recurrent or suspected *enterococcus* infection, other medical and surgical conditions associated with increased risk of infection, Gram positive sepsis, Gram negative sepsis, culture negative sepsis, fungal sepsis, meningococcemia, post-pump syndrome, cardiac stun syndrome, stroke, congestive heart failure, hepatitis, epiglotittis, *E. coli* 0157: H7, malaria, gas gangrene, toxic shock syndrome, preeclampsia, eclampsia, HELP syndrome, mycobacterial tuberculosis, *Pneumocystic carinii*, pneumonia, Leishmaniasis, hemolytic uremic syndrome/thrombotic thrombocytopenic purpura, Dengue hemorrhagic fever, pelvic inflammatory disease, Legionella, Lyme disease, Influenza A, Epstein-Barr virus, encephalitis, inflammatory diseases and autoimmunity including Rheumatoid arthritis, osteoarthritis, progressive systemic sclerosis, systemic lupus erythematosus, inflammatory bowel disease, idiopathic pulmonary fibrosis, sarcoidosis, hypersensitivity pneumonitis, systemic vasculitis, Wegener's granulomatosis, transplants including heart, liver, lung kidney bone marrow, graft-versus-host disease, transplant rejection, sickle cell anemia, nephrotic syndrome, toxicity of agents such as OKT3, cytokine therapy, and cirrhosis.

In some embodiments, the polypeptide or fusion protein of the present invention is particularly suitable for preventing Th17 cell transmigration. Accordingly, the polypeptide or fusion protein of the present invention is particularly suitable for treating Th17 mediated diseases. The term "Th17-mediated disease" is used herein in the broadest sense and includes all diseases and pathological conditions the pathogenesis of which involves abnormalities of Th17 cells. As used herein, the term "Th17 cells" has its general meaning in the art and refers to a subset of T helper cells producing interleukin 17 (IL-17). "A brief history of T(H) 17, the first major revision in the T(H)1/T(H)2 hypothesis of T cell-mediated tissue damage". Nat. Med. 13 (2): 139-145.). The term "IL-17" has its general meaning in the art and refers to the interleukin-17A protein. Typically, Th17 cells are characterized by classical expression of Th cell markers at their cell surface such as CD4, and by the expression of IL17. Typically, as referenced herein, a Th17 cell is a IL-17+ cell. Examples of Th17 mediated diseases include but are not limited to autoimmune diseases, inflammatory diseases, osteoclasia, and transplantation rejection of cells, tissue and organs. In particular, the above-mentioned Th17-mediated diseases may be one or more selected from the group consisting of Behcet's disease, polymyositis/ dermatomyositis, autoimmune cytopenias, autoimmune myocarditis, primary liver cirrhosis, Goodpasture's syndrome, autoimmune meningitis, Sjögren's syndrome, systemic lupus erythematosus, Addison's disease, alopecia greata, ankylosing spondylitis, autoimmune hepatitis, autoimmune mumps, Crohn's disease, insulin-dependent diabetes mellitus, dystrophic epidermolysis bullosa, epididymitis, glomerulonephritis, Graves' disease, Guillain-Barré syndrome, Hashimoto's disease, hemolytic anemia, multiple sclerosis, myasthenia gravis, pemphigus vulgaris, psoriasis, rheumatic fever, rheumatoid arthritis, sarcoidosis, scleroma, spondyloarthropathy, thyroiditis, vasculitis, vitiligo, myxedema, pernicious anemia and ulcerative colitis.

Typically, the polypeptide or fusion protein of the present invention is administered to the subject in a therapeutically effective amount. By a "therapeutically effective amount" is meant a sufficient amount of the polypeptide or fusion protein of the present invention for reaching a therapeutic effect (e.g. treating cancer). It will be understood, however, that the total daily usage of the compounds and compositions of the present invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination or coincidental with the specific polypeptide employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Typically, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, typically from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

In some embodiments, the therapeutic method of the present comprises the steps of i) determining the level of i) determining the level of soluble CD95L in a blood sample obtained from the subject ii) comparing the level determined at step i) with a predetermined reference value and iii) administering the subject with a therapeutically effective amount of the polypeptide or fusion protein of the present invention when the level determined at step i) is higher than the predetermined reference value.

As used herein the term CD95L has its general meaning in the art ant refers to the cognate ligand of CD95 that is a transmembrane protein. As used herein the term "soluble CD95L" has its general meaning in the art and refers to the soluble ligand produced by the cleavage of the transmembrane CD95L (also known as FasL) (Matsuno et al., 2001; Vargo-Gogola et al., 2002; Kiaei et al., 2007; Kirkin et al., 2007; or Schulte et al., 2007). The term "serum CD95L", "soluble CD95L", "metalloprotease-cleaved CD95L" and "cl-CD95L" have the same meaning along the specification.

According to the invention, the measure of the level of soluble CD95L can be performed by a variety of techniques. Typically, the methods may comprise contacting the sample with a binding partner capable of selectively interacting with soluble CD95L in the sample. In some aspects, the binding partners are antibodies, such as, for example, monoclonal antibodies or even aptamers. The aforementioned assays generally involve the binding of the partner (i.e. antibody or aptamer) to a solid support. Solid supports, which can be used in the practice of the present invention include substrates such as nitrocellulose (e.g., in membrane or microtiter well form); polyvinylchloride (e.g., sheets or microtiter wells); polystyrene latex (e.g., beads or microtiter plates); polyvinylidine fluoride; diazotized paper; nylon membranes; activated beads, magnetically responsive beads, and the like. The level of soluble CD95L may be measured by using standard immunodiagnostic techniques, including immunoassays such as competition, direct reaction, or sandwich type assays. Such assays include, but are not limited to, agglutination tests; enzyme-labelled and mediated immunoassays, such as ELISAs; biotin/avidin type assays; radioimmunoassays; immunoelectrophoresis; immunoprecipitation. An exemplary biochemical test for identifying specific proteins employs a standardized test format, such as ELISA test, although the information provided herein may apply to the development of other biochemical or diagnostic tests and is not limited to the development of an ELISA test (see, e.g., Molecular Immunology: A Textbook, edited by Atassi et al. Marcel Dekker Inc., New York and Basel 1984, for a description of ELISA tests). It is understood that commercial assay enzyme-linked immunosorbant assay (ELISA) kits for various plasma constituents are available. Therefore ELISA method can be used, wherein the wells of a microtiter plate are coated with a set of antibodies, which recognize soluble CD95L. A sample containing or suspected of containing soluble CD95L is then added to the coated wells. After a period of incubation sufficient to allow the formation of antibody-antigen complexes, the plate(s) can be washed to remove unbound moieties and a detectably labelled secondary binding molecule added. The secondary binding molecule is allowed to react with any captured sample marker protein, the plate washed and the presence of the secondary binding molecule detected using methods well known in the art. Typically, levels of immunoreactive soluble CD95L in a sample may be measured by an immunometric assay on the basis of a double-antibody "sandwich" technique, with a monoclonal antibody specific for soluble CD95L (Cayman Chemical Company, Ann Arbor, Mich.). According to said embodiment, said means for measuring soluble CD95L level are for example i) a soluble CD95L buffer, ii) a monoclonal antibody that interacts specifically with soluble CD95L, iii) an enzyme-conjugated antibody specific for soluble CD95L and a predetermined reference value of soluble CD95L.

Another object of the present invention relates to a pharmaceutical composition comprising a polypeptide or the fusion protein or the nucleic acid sequence or the expression vector or the host cell according to the invention and a pharmaceutically acceptable carrier. Typically, the polypeptide or the fusion protein or the nucleic acid sequence or the expression vector or the host cell according to the invention may be combined with pharmaceutically acceptable excipients, and optionally sustained-release matrices, such as biodegradable polymers, to form therapeutic compositions. "Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

In the pharmaceutical compositions of the present invention for oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms.

Typically, the pharmaceutical compositions contain vehicles, which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions. The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. Solutions comprising compounds of the present invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms. The polypeptide or fusion protein of the present invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin. Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The preparation of more, or highly concentrated solutions for direct injection is also contemplated, where the use of DMSO as solvent is envisioned to result in extremely rapid penetration, delivering high concentrations of the active agents to a small tumor area. Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. Some variation in dosage will necessarily occur depending on the condition of the subject being treated. The person responsible for administration will, in any event, determine the appropriate dose for the individual subject.

In some embodiments, the polypeptide or fusion protein of the present invention is particularly suitable for use in screening methods for identifying drugs for reducing CD95-mediated cell motility in a subject.

Accordingly a further aspect of the present invention consists of a method for screening a drug for reducing CD95-mediated cell motility comprising the steps consisting of a) determining the ability of a candidate compound to inhibit the interaction between CD95 and a polypeptide or fusion protein of the present invention and b) positively selecting the candidate compound that inhibits said interaction.

At step a), any method suitable for the screening of protein-protein interactions is suitable. Whatever the embodiment of step a) of the screening method, the complete CD95 protein and polypeptide or fusion protein of the present invention may be used as the binding partners. Alternatively, fragments of CD95 protein that include the site of interaction are used. Therefore in some embodiments, the step a) of the screening method of the present invention consists of determining the ability of the candidate compound to inhibit the binding between two polypeptides or fusion protein of the present invention.

In some embodiments, step a) consists in generating physical values which illustrate or not the ability of the candidate compound to inhibit the interaction between the two polypeptides or fusion proteins of the present invention and comparing said values with standard physical values obtained in the same assay performed in the absence of the said candidate compound. The "physical values" that are referred to above may be of various kinds depending of the binding assay that is performed, but notably encompass light absorbance values, radioactive signals and intensity value of fluorescence signal. If after the comparison of the physical values with the standard physical values, it is determined that the said candidate compound modulates the binding between said first polypeptide and said second polypeptide, then the candidate is positively selected at step b).

In some embodiments, the polypeptide or fusion protein of the present invention is labeled with a detectable molecule for the screening purposes. Typically, the detectable molecule may consist of any compound or substance that is detectable by spectroscopic, photochemical, biochemical, immunochemical or chemical means. For example, useful detectable molecules include radioactive substance (including those comprising 32P, 25S, 3H, or 125I), fluorescent dyes (including 5-bromodesosyrudin, fluorescein, acetylaminofluorene or digoxigenin), fluorescent proteins (including GFPs and YFPs), or detectable proteins or peptides (including biotin, polyhistidine tails or other antigen tags like the HA antigen, the FLAG antigen, the c-myc antigen and the DNP antigen). In some embodiments, the detectable molecule is located at, or bound to, an amino acid residue located outside the said amino acid sequence of interest, in order to minimise or prevent any artefact for the binding between said polypeptides or between the candidate compound and or any of the polypeptides.

In some embodiments, the polypeptides of the present invention are fused with a GST tag (Glutathione S-transferase). In this embodiment, the GST moiety of the said fusion protein may be used as detectable molecule. In the said fusion protein, the GST may be located either at the N-terminal end or at the C-terminal end. The GST detectable molecule may be detected when it is subsequently brought into contact with an anti-GST antibody, including with a labelled anti-GST antibody. Anti-GST antibodies labelled with various detectable molecules are easily commercially available.

In some embodiments, the polypeptides of the present invention are fused with a poly-histidine tag. Said polyhistidine tag usually comprises at least four consecutive histidine residues and generally at least six consecutive histidine residues. Such a polypeptide tag may also comprise up to 20 consecutive histidine residues. Said poly-histidine tag may be located either at the N-terminal end or at the C-terminal end. In this embodiment, the poly-histidine tag may be detected when it is subsequently brought into contact with an anti-poly-histidine antibody, including with a labelled anti-poly-histidine antibody. Anti-poly-histidine antibodies labelled with various detectable molecules are easily commercially available.

In some embodiments, the polypeptides of the present invention are fused with a protein moiety consisting of either the DNA binding domain or the activator domain of a transcription factor. Said protein moiety domain of transcription may be located either at the N-terminal end or at the C-terminal end. Such a DNA binding domain may consist of the well-known DNA binding domain of LexA protein originating form *E. Coli*. Moreover said activator domain of a transcription factor may consist of the activator domain of the well-known Gal4 protein originating from yeast.

In some embodiments of the screening method according to the invention, polypeptides or fusion proteins of the present comprise a portion of a transcription factor. In said assay, the binding together of the first and second portions generates a functional transcription factor that binds to a specific regulatory DNA sequence, which in turn induces expression of a reporter DNA sequence, said expression being further detected and/or measured. A positive detection of the expression of said reporter DNA sequence means that an active transcription factor is formed, due to the binding together of said polypeptides or fusion proteins of the present invention. Usually, in a two-hybrid assay, the first and second portion of a transcription factor consist respectively of (i) the DNA binding domain of a transcription factor and (ii) the activator domain of a transcription factor. In some embodiments, the DNA binding domain and the activator domain both originate from the same naturally occurring transcription factor. In some embodiments, the DNA binding domain and the activator domain originate from distinct naturally occurring factors, while, when bound together, these two portions form an active transcription factor. The term "portion" when used herein for transcription factor, encompass complete proteins involved in multi protein transcription factors, as well as specific functional protein domains of a complete transcription factor protein. Therefore in some embodiments of the present invention, step a) of the screening method of the present invention comprises the following steps: (1) providing a host cell expressing:

a first fusion protein between (i) a polypeptide of the present invention and (ii) a first protein portion of transcription factor a second fusion protein between (i) a polypeptide of the present invention and (ii) a second portion of a transcription factor said transcription factor being active on DNA target regulatory sequence when the first and second protein portion are bound together and said host cell also containing a nucleic acid comprising (i) a regulatory DNA sequence that may be activated by said active transcription factor and (ii) a DNA report sequence that is operatively linked to said regulatory sequence (2) bringing said host cell provided at step 1) into contact with a candidate compound to be tested (3) determining the expression level of said DNA reporter sequence The expression level of said DNA reporter sequence that is determined at step (3) above is compared with the expression of said DNA reporter sequence when step (2) is omitted. A different expression level of said DNA reporter sequence in the presence of the candidate compound means that the said candidate compound effectively inhibits the binding between the two polypeptides of the present invention and that said candidate compound may be positively selected a step b) of the screening method.

Suitable host cells include, without limitation, prokaryotic cells (such as bacteria) and eukaryotic cells (such as yeast cells, mammalian cells, insect cells, plant cells, etc.). However preferred host cell are yeast cells and more preferably a *Saccharomyces cerevisiae* cell or a *Schizosaccharomyces pombe* cell. Similar systems of two-hybrid assays are well know in the art and therefore can be used to perform the screening method according to the invention (see. Fields et al. 1989; Vasavada et al. 1991; Fearon et al. 1992; Dang et al., 1991, Chien et al. 1991, U.S. Pat. Nos. 5,283,173, 5,667,973, 5,468,614, 5,525,490 and 5,637,463). For instance, as described in these documents, the Gal4 activator domain can be used for performing the screening method according to the invention. Gal4 consists of two physically discrete modular domains, one acting as the DNA binding domain, the other one functioning as the transcription-activation domain. The yeast expression system described in the foregoing documents takes advantage of this property. The expression of a Gal1-LacZ reporter gene under the control of a Gal4-activated promoter depends on the reconstitution of Gal4 activity via protein-protein interaction. Colonies containing interacting polypeptides are detected with a chromogenic substrate for β-galactosidase. A compete kit (MATCHMAKER, ®) for identifying protein-protein interactions is commercially available from Clontech. In some embodiments, a first polypeptide of the present invention is fused to the DNA binding domain of Gal4 and a second polypeptide of the present invention as above defined is fused to the activation domain of Gal4. The expression of said detectable marker gene may be assessed by quantifying the amount of the corresponding specific mRNA produced. However, usually the detectable marker gene sequence encodes for detectable protein, so that the expression level of the said detectable marker gene is assessed by quantifying the amount of the corresponding protein produced. Techniques for quantifying the amount of mRNA or protein are well known in the art. For example, the detectable marker gene placed under the control of regulatory sequence may consist of the β-galactosidase as above described.

In some embodiments, the first polypeptides or fusion proteins of the present invention are labelled with a fluorescent molecule or substrate. Therefore, the potential alteration effect of the candidate compound to be tested on the binding between the 2 polypeptides or fusion proteins of the present invention is determined by fluorescence quantification.

In some embodiments, the detectable molecule is a protein fragment complementation system, wherein one protein fragment fused to one polypeptide of the present invention is complementary to another protein fragment fused to the other polypeptide of the present invention and complementation of protein fragments generates a measurable signal (protein fragment complementation assay). In some embodiments, the complementary protein fragments generate an active enzyme. In some embodiments, the active enzyme is β-lactamase that can generate a colored product from a substrate such as nitrocefin, a fluorescent product from the substrate such as Fluorocillin Green, or a bioluminescent product (in combination with firefly luciferase) from a substrate such as Bluco (β-lactam-D-luciferin). In some embodiments, the active enzyme is a luciferase that can generate bioluminescence from a substrate such as D-luciferin for firefly luciferase and coelenterazine luciferin for *renilla* and gaussia luciferases.

In some embodiments, the polypeptides of the present invention are labelled with fluorescent molecules that are suitable for performing fluorescence detection and/or quantification for the binding between said polypeptides using fluorescence energy transfer (FRET) assay or BRET (bioluminescence resonance energy transfer).

In some embodiments, the donor detectable molecule is a bioluminescent enzyme that can transfer resonance energy (BRET). For example, a luciferase enzyme typically generates light upon oxidation of its substrate, but can also transfer the energy to a fluorophore that is in proximity. In some embodiments, the bioluminescent enzyme is expressed as a fusion protein with a first polypeptide of the present invention. In some embodiments, the bioluminescent protein is firefly, *renilla*, or gaussia luciferase. In some embodiments, the acceptor fluorophore is a fluorescent protein that is fused to a second polypeptide of the present invention. In some embodiments, the acceptor fluorophore is an organic or inorganic.

In some embodiments, a first polypeptide of the present invention is labelled with a first fluorophore substance and a second polypeptide of the present invention is labelled with a second fluorophore substance. The first fluorophore substance may have a wavelength value that is substantially equal to the excitation wavelength value of the second fluorophore, whereby the bind of said first and second polypeptides is detected by measuring the fluorescence signal intensity emitted at the emission wavelength of the second fluorophore substance. Alternatively, the second fluorophore substance may also have an emission wavelength value of the first fluorophore, whereby the binding of said and second polypeptides is detected by measuring the fluorescence signal intensity emitted at the wavelength of the first fluorophore substance. The fluorophores used may be of various suitable kinds, such as the well-known lanthanide chelates. These chelates have been described as having chemical stability, long-lived fluorescence (greater than 0.1 ms lifetime) after bioconjugation and significant energy-transfer in specificity bio affinity assay. Document U.S. Pat. No. 5,162,508 discloses bipyridine cryptates. Polycarboxylate chelators with TEKES type photosensitizers (EP0203047A1) and terpyridine type photosensitizers (EP0649020A1) are known. Document WO96/00901 discloses diethylenetriaminepentaacetic acid (DPTA) chelates which used carbostyril as sensitizer. Additional DPT chelates with other sensitizer and other tracer metal are known for diagnostic or imaging uses (e.g., EP0450742A1).

In some embodiments, the fluorescence assay performed at step a) of the screening method consists of a Homogeneous Time Resolved Fluorescence (HTRF) assay, such as described in document WO 00/01663 or U.S. Pat. No. 6,740,756, the entire content of both documents being herein incorporated by reference. HTRF is a TR-FRET based technology that uses the principles of both TRF (time-resolved fluorescence) and FRET. More specifically, the one skilled in the art may use a HTRF assay based on the time-resolved amplified cryptate emission (TRACE) technology as described in Leblanc et al. (2002). The HTRF donor fluorophore is Europium Cryptate, which has the long-lived emissions of lanthanides coupled with the stability of cryptate encapsulation. XL665, a modified allophycocyanin purified from red algae, is the HTRF primary acceptor fluorophore. When these two fluorophores are brought together by a biomolecular interaction, a portion of the energy captured by the Cryptate during excitation is released through fluorescence emission at 620 nm, while the remaining energy is transferred to XL665. This energy is then released by XL665 as specific fluorescence at 665 nm. Light at 665 nm is emitted only through FRET with Europium. Because Europium Cryptate is always present in the assay, light at 620 nm is detected even when the biomolecular interaction does not bring XL665 within close proximity.

Therefore in some embodiments, step a) of the screening method may therefore comprises the steps consisting of:
(1) bringing into contact a pre-assay sample comprising:
  a first polypeptide of the present invention fused to a first antigen,
  a second polypeptide of the present invention fused to a second antigen
  a candidate compound to be tested (2) adding to the said pre assay sample of step (2):
at least one antibody labelled with a European Cryptate which is specifically directed against the first said antigen
at least one antibody labelled with XL665 directed against the second said antigen
(3) illuminating the assay sample of step (2) at the excitation wavelength of the said European Cryptate
(4) detecting and/or quantifying the fluorescence signal emitted at the XL665 emission wavelength
(5) comparing the fluorescence signal obtained at step (4) to the fluorescence obtained wherein pre assay sample of step (1) is prepared in the absence of the candidate compound to be tested.

If at step (5) as above described, the intensity value of the fluorescence signal is different (lower or higher) than the intensity value of the fluorescence signal found when pre assay sample of step (1) is prepared in the absence of the candidate compound to be tested, then the candidate compound may be positively selected at step b) of the screening method. Antibodies labelled with a European Cryptate or labelled with XL665 can be directed against different antigens of interest including GST, poly-histidine tail, DNP, c-myx, HA antigen and FLAG which include. Such antibodies encompass those which are commercially available from CisBio (Bedford, Mass., USA), and notably those referred to as 61GSTKLA or 61HISKLB respectively.

The candidate compounds that have been positively selected at the end of any one of the embodiments of the in vitro screening which has been described previously in the present specification may be subjected to further selection steps in view of further assaying its properties on the CD95-mediated cell motility (e.g, CD95-mediated Ca2+ response or cell migration). For this purpose, the candidate compounds that have been positively selected with the general in vitro screening method as above described may be further selected for their to reduce or inhibit CD95-mediated Ca2+ response and/or cell migration induced by soluble CD95L. Thus, in some embodiments, the screening method of the present invention comprises the steps of: i) screening for candidate compounds that inhibit the interaction between CD95 and the polypeptide or fusion protein of the present invention, by performing the in vitro screening method as above described and ii) screening the candidate compounds positively selected at the end of step i) for their ability to reduce CD95-mediated Ca2+ response and/or CD95-mediated cell motility (e.g. cell migration mediated by soluble CD95L). In some embodiments, the step ii) of said screening method comprises the following steps: (1) bringing into contact a cell with a candidate compound that has been positively selected at the end of step i), (2) determining the capacity of compound to inhibit or reduce CD95-mediated Ca2+ response and/or cell migration induced by soluble CD95L and (3) comparing the CD95-mediated Ca2+ response and/or cell migration determined at step (2) with the CD95-mediated Ca2+ response and/or cell migration determined when step (1) is performed in the absence of the said positively selected candidate compound, and (4) positively selecting the candidate compound when the CD95-mediated Ca2+ response and/or cell migration determined at step (2) is lower than the CD95-mediated Ca2+ response and/or cell migration determined when step (1) is performed in the absence of the said candidate compound. In some embodiments, the cell is selected from the group consisting of T cell and cancer cells (e.g. breast cancer cells such as TNBC cells (MDA-MB-231)). Typically a migration assay or a CD95-mediated Ca2+ response assay as described in the EXAMPLE may be used. Step (1) as above described may be performed by adding an amount of the candidate compound to be tested to the culture medium. Usually, a plurality of culture samples are prepared, so as to add increasing amounts of the candidate compound to be tested in distinct culture samples. Generally, at least one culture sample without candidate compound is also prepared as a negative control for further comparison. Optionally, at least one culture sample with an already known agent that reduces the CD95-mediated Ca2+ response and/or cell migration is also prepared as a positive control for standardization of the method. Therefore, step (3) may be performed by comparing the percentage of cells wherein the CD95-mediated Ca2+ response and/or cell migration is modulated obtained for the cell cultures incubated with the candidate compound to be tested with the percentage of cells wherein the CD95-mediated Ca2+ response and/or cell migration is modulated obtained for the negative control cell cultures without the candidate compound. Illustratively, the efficiency of the candidate compound may be assessed by comparing (i) the percentage of cells wherein the CD95-mediated Ca2+ response and/or cell migration is reduced with (ii) the percentage of cells wherein the CD95-mediated Ca2+ response and/or cell migration is reduced measured in the supernatant of the cell cultures that were incubated with the known agent that modulates the CD95-mediated Ca2+ response and/or cell migration. Further illustratively, the efficiency of the candidate compound may be assessed by determining for which amount of the candidate compound added to the cell cultures the percentage of cells wherein the CD95-mediated Ca2+ response and/or cell migration is reduced is close or higher than the percentage of cells wherein the CD95-mediated Ca2+ response and/or cell migration is reduced with the known agent that inhibits or reduces the CD95-mediated Ca2+ response and/or cell migration.

In some embodiments, the candidate compound of may be selected from the group consisting of peptides, peptidomimetics, small organic molecules, or nucleic acids. For example the candidate compound according to the invention may be selected from a library of compounds previously synthetized, or a library of compounds for which the structure is determined in a database, or from a library of compounds that have been synthetized de novo. In a particular embodiment, the candidate compound may be selected form small organic molecules. As used herein, the term "small organic molecule" refers to a molecule of size comparable to those organic molecules generally sued in pharmaceuticals. The term excludes biological macromolecules (e.g.; proteins, nucleic acids, etc.); preferred small organic molecules range in size up to 2000 Da, and most preferably up to about 1000 Da.

The invention will be further illustrated by the following figures and examples. However, these examples and figures should not be interpreted in any way as limiting the scope of the present invention.

FIGURES

FIG. 1: Cleaved-CD95L mobilizes Calcium ions from both extracellular and intracellular compartments by mechanisms involving $Ca^{2+}$ channels, PLCγ, IP3 and Ryanodine Receptors. $[Ca^{2+}]_i$, was monitored via the ratio F340 nm/F380 nm (relative $[Ca^{2+}]$cytosolic) using Fura2 as fluorescent probe. Data represent mean+/−SD of at least 60 cells (3 independent experiments). Jurkat cells were stimulated with 100 ng/ml cl-CD95L (black arrow). A. Cells were bathed in a 2 mM Ca$^{2+}$-containing medium (black squares) or in a Ca$^{2+}$-free medium (open circles). The transient Ca$^{2+}$ increase occurring in Ca$^{2+}$-free medium (open circles) corresponds to the release of calcium ions stored in intracellular compartments. The plateau phase observed in 2 mM Ca$^{2+}$-containing medium, and disappearing in Ca$^{2+}$-free medium is mainly due to calcium influx from the extracellular space. B. In PLCγ1−/− Jurkat cells (open circles), cl-CD95L failed to induce the initial, transient increase in [Ca$^{2+}$]i, which is restored when PLCγ1 is reintroduced in the PLCγ1−/− cells (black squares). C. Jurkat cells were pretreated (2 μM, 20 minutes) with Xestospongin C (XestoC, open circles), a membrane permeable, potent IP3 receptors blocker. Such a treatment again, completely blocked the initial component of the calcium response. D. Jurkat cells were pretreated (20 minutes) with high concentrations (10 μM) of Ryanodine (Rya, open triangle), in order to block Ryanodine receptors, or with Ryanodine and Xestospongin C (XestoC, open circle) to block both ryanodine and IP3 receptors. Rya did not reduce the initial peak but blocked the plateau phase. Combination of Rya and XestoC abolished the CD95-mediated Ca$^{2+}$ response.

Figure 2:
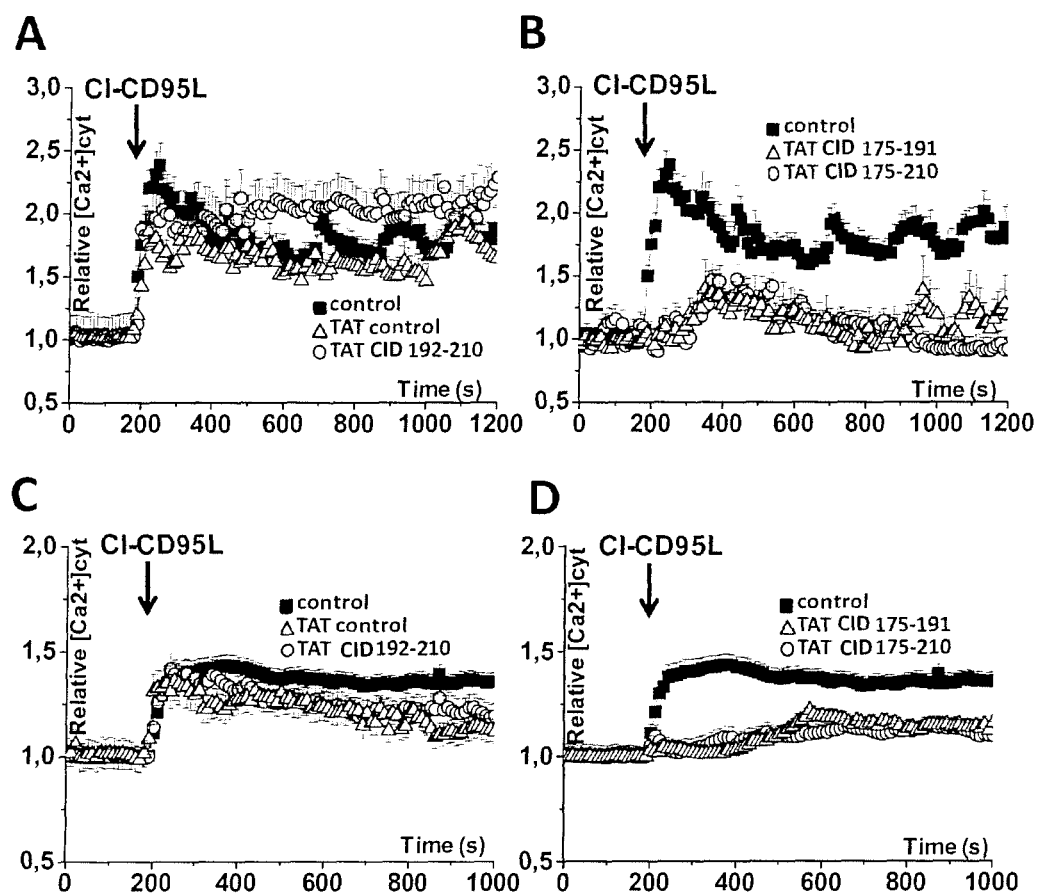

FIG. 2: TAT CID 175-210 and TAT CID 175-191 impair the PLCγ/IP3-dependent calcium response to cl-CD95L. [Ca$^{2+}$]$_i$ was monitored via the ratio F340 nm/F380 nm (relative [Ca$^{2+}$]cytosolic) using Fura2 as fluorescent probe. Data represent mean+/−SD of at least 60 cells (3 independent experiments). Jurkat (A and B) and activated PBL (C and D) were stimulated with 100 ng/ml Cl-CD95L (black arrow). A. Jurkat were pre-incubated with a TAT peptide control (1 hr, 10 μM, open triangle) or with a TAT peptide corresponding to the aa 192-210 of the death receptor CD95 (1 hr, 10 μM, open circles) or not (control, black squares). The treatments did not significantly modify the calcium response to cl-CD95L. B. Jurkat were pre-incubated with a TAT peptide corresponding to the aa 175-210 of the death receptor CD95 (1 hr, 10 μM, open circles) or with a TAT peptide corresponding to the aa 175-191 of the death receptor CD95 (1 hr, 10 μM, open triangles) or not (black squares). Both treatments greatly reduced the calcium response to cl-CD95L, particularly the initial peak. C. Activated PBL were pre-incubated with the TAT peptide control (1 hr, 10 μM, open triangles) or with the TAT peptide corresponding to the aa 192-210 of the death receptor CD95 (1 hr, 10 μM, open circles) or not (control, black squares). The treatments did not significantly modify the calcium response to Cl-CD95L. D. Activated PBL were pre-incubated with a TAT peptide corresponding to the aa 175-210 of the death receptor CD95 (1 hr, 10 μM, open circles) or with a TAT peptide corresponding to the aa 175-191 of the death receptor CD95 (1 hr, 10 μM, open triangles) or not (black squares). Both treatments greatly reduced the calcium response to cl-CD95L, particularly the initial peak.

Figure 3:
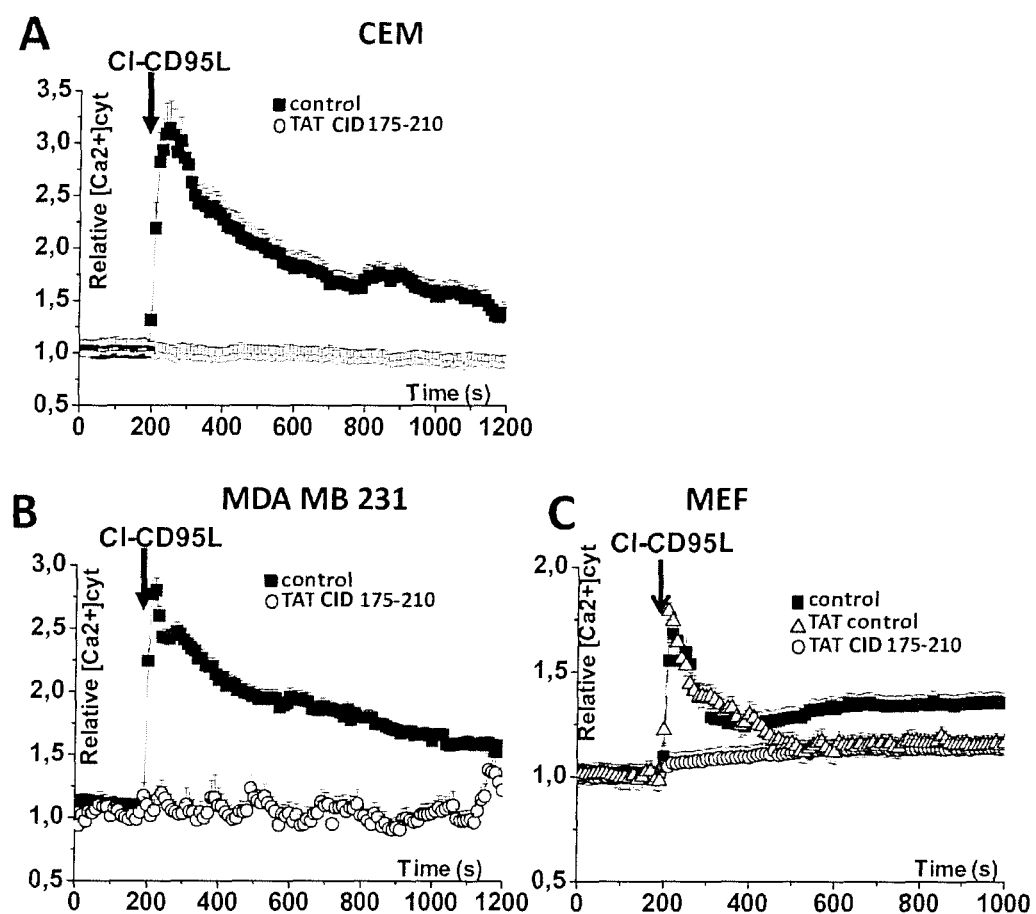

FIG. 3: TAT CID 175-210 is effective in various cell models. [Ca$^{2+}$]$_i$ was monitored via the ratio F340 nm/F380 nm (relative [Ca$^{2+}$]cytosolic) using Fura2 as fluorescent probe. Data represent mean+/−SD of at least 60 cells (3 independent experiments). CEM (A), MDA MB 231(B) and MEF (C) were stimulated with 100 ng/ml cl-CD95L (black arrow). A and B. CEM and MDA MB 231 cells were pre-incubated with a TAT peptide corresponding to the aa 175-210 of the death receptor CD95 (1 hr, 10 μM, open circle). The treatment (open circles) completely abolished the calcium response in both cell types. C. MEFs were pre-incubated with the TAT peptide corresponding to the aa 175-210 of the death receptor CD95 (1 hr, 10 μM, open circle) or with the TAT peptide control (1 hr, 10 μM, open triangles). If the latter did not modify the initial phase, the former blocked it.

Figure 4:
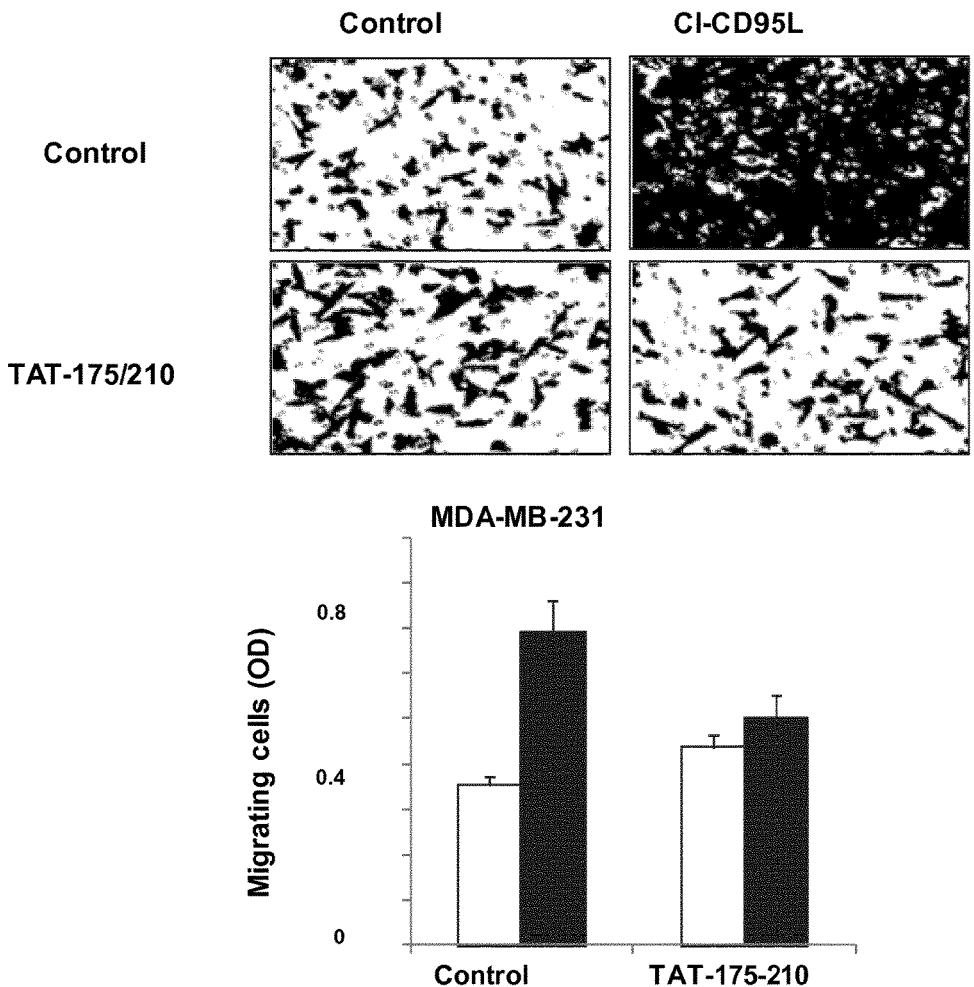

FIG. 4: TAT CID 175-210 inhibits migration of triple cell negative cancer cells. The triple negative breast cancer cell line MDA-MB-231 was pre-incubated for 1 hour with 10 μM of CID 175-210 and cell migration was assessed using the Boyden chamber assay in the presence or absence of cl-CD95L (100 ng/mL) for 24 h. Migrating cells were stained with Giemsa. For each experiment, five images of random fields were acquired.

FIG. 5. High amounts of serum CD95L in SLE patients correspond to a homotrimeric ligand inducing endothelial transmigration of activated T lymphocytes. A. Soluble CD95L was dosed by ELISA in sera of newly diagnosed SLE patients and healthy donors. *** indicates P≤0.0001 using a two-tailed student's t test. B. Sera from SLE patient were fractionated using size exclusion S-300-HR Sephacryl columns and CD95L was dosed by ELISA. Inset: CD95L was immunoprecipitated in fractions 40-46 and 76-78 and loaded in a 12% SDS-PAGE. Anti-CD95L immunoblot is depicted. C. Activated PBLs from healthy donors were incubated in presence of gel filtration fractions obtained in B and endothelial transmigration was assessed as described in *Materials and Methods*. Where indicated, fractions 76-78 were pre-incubated 30 minutes with the antagonist anti-CD95L mAb NOK-1 (10 μg/ml). D. CD95L, IL17 and CD4 expression levels were analyzed by Immunohistochemistry in inflamed skins of lupus patients or in healthy subjects (mammectomy). Numbers correspond to different patients. E. Densitometric analyses of CD95L and IL17 staining depicted in D revealed that the expression levels of these two markers vary in a correlated manner. F. The indicated human T-cell subsets were subject to transmigration assay in presence of sera taken from SLE patients or healthy donor as controls. Data were analyzed using Mann-Whitney U-test. ***P<0.001 G. Human T-cell subsets were subject to transmigration assay as above except in the lower chamber Fas-Fc was added at increasing concentrations in parallel with cl-CD95L. Data represent the mean of 4-5 individual donors±SD and were analyzed using a 2-way Anova. H. Transmigration of CD4 T-cell subsets was analyzed in Boyden chambers in presence or absence of cl-CD95L (200 ng/ml). I. Transmigration of human regulatory T-cells and Th17 cells was assessed by Boyden Chamber assay in presence or absence of cl-CD95L. Data was analyzed using a 2-way Anova. P values<0.05 was considered significant; *P<0.05, ***P<0.001

Figure 6:
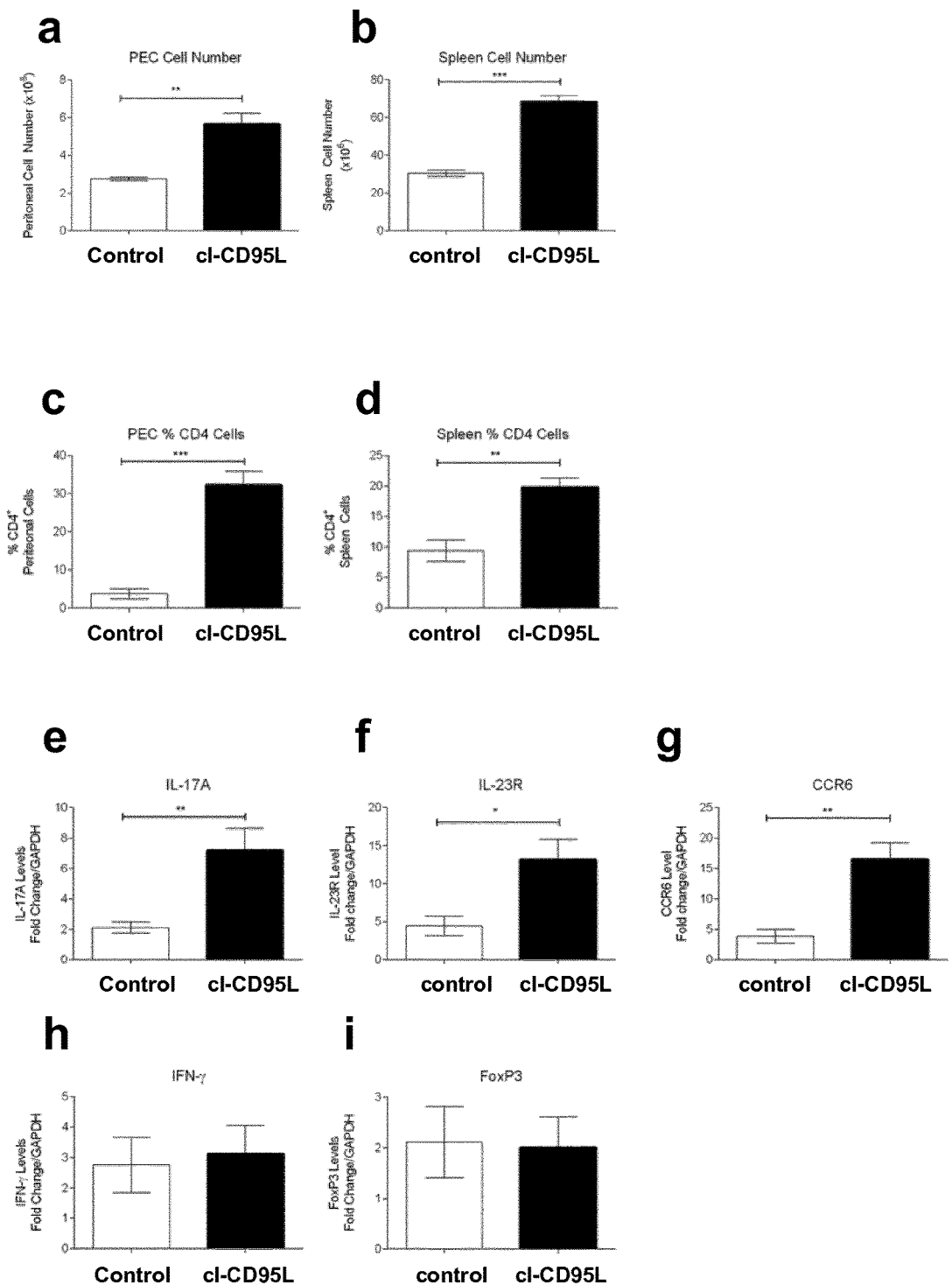

FIG. 6. In vivo administration of cl-CD95L preferentially attracts Th17 cells. Mice were injected once with cl-CD95L (200 ng) or vehicle, and 24 hrs later subject to examination. (A-B). Total cell counts for the peritoneal cavity (A) and spleen (B) were performed. (C-D). Differential white blood cell count was performed 24 hrs post injection. Peritoneal Exudate Cells (PEC) (C) and spleen (D) cells were subject to flow cytometry analysis to identify the percentage of infiltrated CD4$^+$ cells. (E-I). PEC CD4$^+$ cells were purified by AutoMACS separation and RNA prepared. Cells were subject to real-time PCR for (E) IL-17A, (F) IL-23R, (G) CCR6, (H) IFN-γ, and (I) FoxP3. Data presented are averages of groups of 6 mice±SD, with experiments repeated twice. Data were analyzed using the students t-Test, P values <0.05 was considered significant; *P<0.05, P<0.01, *P<0.001.

FIG. 7. CD95 implements a Death Domain-independent Ca$^{2+}$ response. A. CEM cells were stimulated with CD95L (100 ng/mL) and CD95 was immunoprecipitated. The immune complex was resolved by SDS/PAGE, and the indicated immunoblottings were performed. Total lysates were loaded as control. B. Parental Jurkat T cells, PLC-γ1-deficient and its PLC-γ1-reconstituted counterparts were loaded with the $Ca^{2+}$ probe FuraPE3-AM (1 μM) and then stimulated with cl-CD95L (100 ng/mL, black arrow). Ratio images (F340/F380, R) were taken every 10 s and were normalized vs pre-stimulated values ($R_0$). Data represent mean ±SD of $R/R_0$ measured in n cells. Inset: PLCγ1-deficient Jurkat cells or its reconstituted counterpart was lysed and the expression levels of PLCγ1 and CD95 were evaluated by immunoblotting. Tubulin was used as a loading control. C. Cells were loaded with the $Ca^{2+}$ probe FuraPE3-AM (1 μM) and then stimulated with cl-CD95L (100ng/ml). Data were analyzed as described in B. Inset: Parental Jurkat cells (A3) or its counterparts lacking either FADD or caspase-8 were lysed and the expression levels of CD95, FADD and Caspase-8 were evaluated by immunoblotting. D. Representation of the different CD95 constructions. E. CEM-IRC cells expressing GFP alone or GFP-fused CD95 constructs shown in D, were loaded with the $Ca^{2+}$ probe fluo2-AM (1 μM). The cells were then stimulated with cl-CD95L (100 ng/mL; black arrow) and $[Ca^{2+}]_i$ was monitored via the ratio $F/F_0$ (relative $Ca^{2+}_{[CYT]}$). Data represent mean ±SD of $F/F_0$ measured in n cells.

FIG. 8. The CD95-mediated $Ca^{2+}$ signal stems from amino-acid residues 175 to 210 in CD95. A. HEK cells were co-transfected with the GFP-fused CD95 constructions and wild type PLCγ1. Twenty-four hours after transfection, CD95 expression level in these cells was evaluated by flow cytometry. B. Cells in A were stimulated with CD95L (100 ng/mL) and CD95 was immunoprecipitated. The immune complex was resolved by SDS-PAGE, and the indicated immunoblotting was performed. Total lysates were loaded as a control. C. Left Panel: HEK cells were co-transfected with PLCγ1 and CID-mCherry or mCherry alone. After 24 h, cells were lysed and PLCγ1 was immunoprecipitated. The immune complex was resolved by SDS/PAGE, and the indicated immunoblottings were performed. Total lysates were loaded as a control. Right Panel: HEK cells were co-transfected with PLCγ1 and CID-mCherry or mCherry alone. After 24 h, cells were stimulated in presence or absence of CD95L (100 ng/mL) and CD95 was immunoprecipitated. The immune complex was resolved by SDS-PAGE, and the indicated immunoblotting was performed. Total lysates were loaded as a control. D. Upper panel; protein sequences of TAT control (SEQ ID NO: 5) and TAT-CID (SEQ ID NO: 6). TAT Domain sequences are identified within bracket (SEQ ID NO: 4). Lower panel; The leukemic T cell line CEM was pre-incubated for 1 h with 10 μM of TAT-control or TAT-CID and then stimulated in presence or absence of cl-CD95L (100 ng/mL) for the indicated times. Cells were lysed and CD95 was immunoprecipitated. The immune complex was resolved by SDS-PAGE, and the indicated immunoblotting was performed. Total lysates were loaded as a control. E. Jurkat and CEM were loaded with FuraPE3-AM(1 μM), pretreated for 1 h with 10 μM of TAT-control or TAT-CID and then stimulated with 100 ng/ml of cl-CD95L (black arrow). Ratio images were taken every 10 s and were normalized vs pre-stimulated values. F. Human PBLs from healthy donors were loaded with furaPE3-AM (1 μM) pretreated for 1 h with 10 μM of TAT-control or TAT-CID or with the IP3R inhibitor Xestospongin C (positive control, 1 μM, 1 h) and then stimulated with 100 ng/ml of cl-CD95L (black arrow). Ratio values (R) were normalized vs pre-stimulated values ($R_0$). Data represent mean ±SD of $R/R_0$ measured in n cells.

Figure 9:
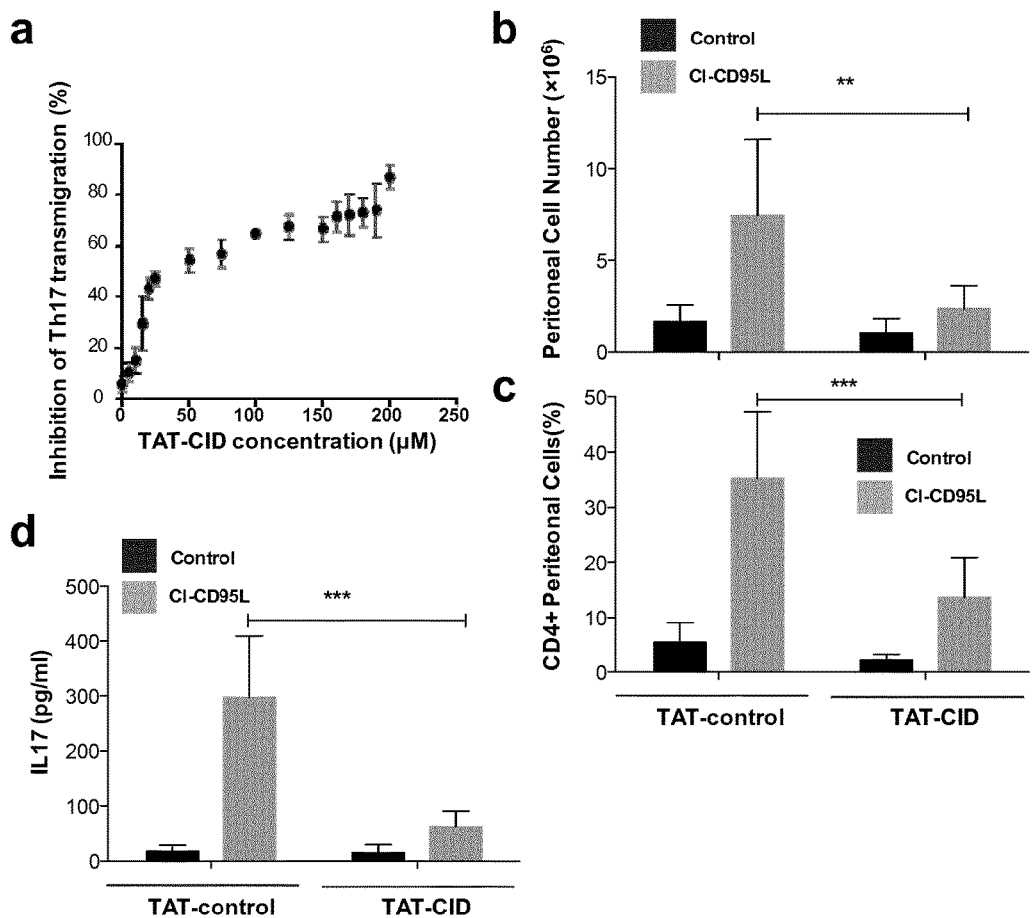

FIG. 9. TAT-CID is an inhibitor of the cl-CD95L-induced Th17 cell accumulation in organs. A. Mouse Th17 cell transmigration was monitored by Boyden Chamber assay in presence or absence of the indicated concentrations of the TAT-CID peptide. B-D. C57BL/6 mice were injected with 40 mg/kg of TAT-control or TAT-CID two hours prior to IP injection cl-CD95L (200 ng) or vehicle, and 24 hours later subject to examination. B. Total cell counts for the peritoneal cavity was performed. C. Peritoneal Exudate Cells (PEC) were subject to flow cytometry analysis to identify the percentage of infiltrated $CD4^+CD62L^-$ T-cells. D. IL-17A levels in the peritoneal cavity were quantified by ELISA. Statistical analysis was performed using a 2-way Anova p-values indicated are p<0.01, *p<0.001.

EXAMPLE 1

Cells were loaded with Fura2-AM (1 μM) at resting temperature for 30 min in Hank's Balanced Salt Solution (HBSS). After washing with HBSS, the cells were incubated for 15 min in the absence of Fura2-AM to complete de-esterification of the dye. Cells were placed in a thermostated chamber (37° C.) of an inverted epifluorescence microscope (Olympus IX70) equipped with a ×40, UApo/340-1.15 W water-immersion objective (Olympus), and fluorescence micrograph images were captured at 510 nm and at 12-bit resolution by a fast-scan camera (CoolSNAP fx Monochrome, Photometrics). To minimize UV light exposure, 4×4 binning function was used. Fura2-AM was alternately excited at 340 and 380 nm, and ratios of the resulting images (excitations at 340 and 380 nm and emission filter at 520 nm) were produced at constant intervals (5 s or 10 s according to the stimulus). Fura-2 ratio ($F_{ratio}$ 340/380) images were displayed and the $F_{ratio}$ values from the regions of interest (ROIs) drawn on individual cells were monitored during the experiments and analyzed later offline with Universal Imaging software, including Metafluor and Metamorph. Each experiment was independently repeated 3 times, and for each experimental condition, we displayed an average of more than 20 single-cell traces. Fluorescent images were pseudocolored using the IMD display mode in MetaFluor and assembled without further manipulation in Photoshop (Adobe). Raw data were acquired with Meta-Fluor and graphed in Origin (OriginLab). $[Ca^{2+}]_i$ was calculated using the following equation: $[Ca^{2+}]_i = K_d(R-R_{min})/(R-R_{max}) \times Sf2/Sf1$, where $K_d$ is the Fura2-AM dissociation constant at the two excitation wavelengths ($F_{340}/F_{380}$); $R_{min}$ is the fluorescence ratio in the presence of minimal calcium, obtained by chelating $Ca^{2+}$ with 10 mM EGTA; $R_{max}$ is the fluorescence ratio in the presence of excess calcium, obtained by treating cells with 1 μM ionomycin; Sf2 is the fluorescence of the $Ca^{2+}$-free form; and Sf1 is the fluorescence of the $Ca^{2+}$-bound form of Fura2-AM at excitation wavelengths of 380 and 340 nm, respectively. In some experiments cells were placed in a $Ca^{2+}$-free medium consisting of the HBSS described above in which $CaCl_2$ was omitted and 100 μM EGTA was added in order to chelate residual $Ca^{2+}$ ions. This medium was added to the cells just before recording to avoid leak of the intracellular calcium stores. Results are shown in FIGS. 1-3.

EXAMPLE 2

Boyden chambers contained membranes with a pore size of 8 μm (Millipore, Molsheim, France). After hydration of the membranes, breast cancer cells ($10^5$ cells per chamber) were added to the top chamber in low serum (1%)-containing medium. The bottom chamber was filled with low serum (1%)-containing medium in the presence or absence of cl-CD95L (100 ng/mL). Cells were cultured for 24 h at 37° C. To quantify migration, cells were mechanically removed from the top-side of the membrane using a cotton-tipped swab, and migrating cells from the reverse side were fixed with methanol and stained with Giemsa. For each experiment, five representative pictures were taken for each insert, then cells were lyzed and absorbance at 560 nm correlated to the amount of Giemsa stain was measured. Results are shown in FIG. 4.

EXAMPLE 3

Methods

Patients and Ethics Statement

SLE patients fulfilled four or more of the 1982 revised ACR criteria for the disease. All clinical investigations were conducted according to the principles expressed in the Declaration of Helsinki. Blood was sampled from patients diagnosed with SLE after written consent was obtained from each individual. This study was approved by institutional review board at the Centre Hospitalier Universitaire de Bordeaux.

Antibodies Other Reagents

PHA, 3-[4,5-dimethylthiazol-2-yl]-2,5-diphenyltetrazolium bromide (MTT), protease and phosphatase inhibitors were purchased from Sigma-Aldrich (L'Isle-d'Abeau-Chesnes, France). Anti-CD95L mAb was from Cell Signaling Technology (Boston, Mass., USA). Recombinant IL-2 was obtained from PeproTech Inc. (Rocky Hill, N.J., USA). Anti-PLCγ1 was purchased from Millipore (St Quentin en Yvelines, France). Anti-CD95 mAbs (APO1-3) came from Enzo Life Sciences (Villeurbanne). PE-conjugated anti-human CD95 (DX2) mAb, anti-human FADD mAb (clone1), neutralizing anti-CD95L mAb (Nok1) were provided by BD Biosciences (Le Pont de Claix, France). Anti-caspase-8 (C15) and anti-Fas (C-20) mAbs were from Santa Cruz Biotechnology (Heidelberg, Germany). CD95-Fc, neutralizing anti-ICAM-1 and E-selectin mAbs.

Plasmids and Constructs

GFP-tagged human CD95 (hCD95) constructs were obtained by PCR and inserted in frame between the Nhe1 and EcoR1 sites of pEGFP-N1 (Clontech). Note that for all CD95 constructs the numbering takes into consideration the subtraction of 16 amino-acid of the signal peptide. Substitution of the cysteine at position 183 by a valine in hCD95$^{(1-210)}$ was performed using the Quickchange Lightning Site-directed Mutagenesis kit (Agilent Technologies, Les Ulis, France) according to manufacturer instructions. The CID-mCHERRY construct was obtained by PCR amplifying the hCD95 sequence coding for the residues 175 to 210. The resulting fragment was inserted between the EcoR1 and BamH1 site of a pmCHERRY-N1 vector. Mouse full length CD95 (mCD95) was kindly provided by Dr Pascal Schneider (Universite de Lausanne, Lausanne, Switzerland). The mCD95 sequence lacking the signal peptide (SP—residues 1-21) was amplified by PCR. After digestion by BamHI/EcoRI, the amplicon was inserted into pcDNA3.1(+) vector in frame with SP sequence of the influenza virus hemagglutinin protein followed by a flag tag sequence and a 6 amino acid linker. The pTriEx-4 vector encoding for Myc-tagged full-length human PLCγ1 was a gift from Dr. Matilda Katan (Chester Beatty Laboratories, The Institute of Cancer Research, London, United Kingdom). Plasmids coding for full length CD95L and the secreted IgCD95L have been described elsewhere (Tauzin et al., 2011). All constructs were validated by sequencing on both strands (GATC Biotech, Constance, Germany).

Cell Lines and Peripheral Blood Lymphocytes

All cells were purchased from ATCC (Molsheim Cedex, France). T leukemic cell lines CEM, H9 and Jurkat were cultured in RPMI supplemented with 8% heat-inactivated FCS (v/v) and 2 mM L-glutamine at 37° C. in a 5% CO2 incubator. CEM-IRC cell expressing a low amount of plasma membrane CD95 was described in (Beneteau et al., 2007; Beneteau et al., 2008). HEK293 cells were cultured in DMEM supplemented with 8% heat-inactivated FCS and 2 mM L-glutamine at 37° C. in a 5% CO2 incubator. PBMCs (peripheral blood mononuclear cells) from healthy donors were isolated by Ficoll centrifugation, washed twice in PBS. Monocytes were removed by a 2 hours adherence step and the naive PBLs (peripheral blood lymphocytes) were incubated overnight in RPMI supplemented with 1 µg/ml of PHA. Cells were washed extensively and incubated in the culture medium supplemented with 100 units/ml of recombinant IL-2 for 5 days. Human umbilical vein endothelial cell (HUVEC) (Jaffe et al., 1973) were grown in human endothelial serum free medium 200 supplemented with LSGS (Low serum growth supplement) (Invitrogen, Cergy Pontoise, France). CEM-IRC cells were electroporated using BTM-830 electroporation generator (BTX Instrument Division, Harvard Apparatus) with 10 µg of DNA. 24 hours after electroporation, cells were treated for one week with 1 mg/mL of neomycin and then clones were isolated using limiting dilution.

Immunohistocytology

Skins from lupus patients were embedded in paraffin and cut into 4 µm sections. For CD4, CD8 and IL17 detection, Immunohistochemical staining was performed on the Discovery Automated IHC stainer using the Ventana OmniMap detection kit (Ventana Medical Systems, Tucson, Ariz., USA). The slides were rinsed with Ventana Tris-based Reaction buffer (Roche). Following deparaffination with Ventana EZ Prep solution (Roche) at 75° C. for 8 min, antigen retrieval was performed using Ventana proprietary, Tris-based buffer solution CC1 (pH8) antibody, at 95° C. to 100° C. for 48 min. Endogen peroxidase was blocked with Inhibitor-D 3% H2O2 (Ventana) for 10 min at 37° C. After rinsing, slides were incubated at 37° C. for 60 min with IL17 (Bioss), CD4 and CD8 (Dako), and secondary antibody: OmniMap HRP for 32 min (Roche). Signal enhancement was performed using the Ventana ChromoMap Kit Slides (biotin free detection system). For CD95L (BD Pharmigen) detection, antigen retrieval was performed using antigen unmasking solution pH 9 (Vector) at 95° C. for 40 min and endogenous peroxidase was blocked using 3% w/v hydrogen peroxide in methanol for 15 min. Slides were incubated in 5% BSA for 30 min at RT and then stained overnight at 4° C. Tissue sections were incubated with Envision+ system HRP-conjugated secondary antibodies for 30 min at RT and labeling was visualized by adding liquid DAB+. Sections were counterstained (hematoxylin) and mounted with DPX mounting medium. Using ImageJ software (IHC toolbox), densitometry analysis was undertaken on scanned slides to evaluate the amount of the different markers. The mean area for each marker was assessed and we determined if a correlation existed between the quantities of IL17-expressing cells and CD8$^+$ T cells and the expression level of CD95L.

Mouse and Human CD4$^+$ T-Cell Subset Generation

Animal experiments were subject to ethical review by the University of Nottingham were appropriate and conducted using PPL 40/3412 in accordance with the UK Home Office guidance and under ASPA (1986). For the generation of murine T-cell subsets, spleens were removed from C57Bl/6 mice and single cell suspensions prepared. CD4+CD62L+ naïve cells were isolated using Miltenyi Biotec microbeads. Naïve human CD4+ T-cells were prepared using the Miltenyi Biotec naïve CD4+ T-cell isolation kit II, which are sorted produced a 99% pure population of CD4+CD45RA+ cells. Purified cells were cultured in complete IMDM media all with α-CD3 (1 μg/ml), α-CD28 (2 μg/ml), and as follows; Th1 cells IL-12 (10 ng/ml) with α-IL-4 (10 μg/ml), Th2 cells IL-4 (10 ng/ml) and α-IFN-γ (10 μg/ml), Th17 cells Il-6 (10 ng/ml), TGF-β1 (2 ng/ml), α-IFN-γ (10 μg/ml) with α-IL-4 (10 μg/ml), and Tregs IL-2 (10 ng/ml) TGF-β1 (5 ng/ml), α-IFN-γ (10 μg/ml) and α-IL-4 (10 μg/ml). Cells were converted to T-cell subsets over five days as outlined above. All cytokines were supplied by PeproTech (London, UK). Mouse CD3 (clone 2C11); human CD3 (UCHT1); mouse CD28 (37.51); human CD28 (CD28.2); mouse IL-4 (11B11); human IL-4 (MP4-25D2); mouse IFN-γ (XMG1.2); human IFN-γ B27 came from BD Pharmigen.

In Vivo Administration of Cl-CD95L

Female C57BL/6 mice (Harlan UK) aged between 8-10 weeks were placed in groups of 6 and administered IP. Twenty-four hours following injection, mice were sacrificed and periteonial cavities were washed with 5 ml of PBS/2% FCS, blood smears were prepared, and spleens were collected. Blood smears and cytospins of periteonal cells (PECs) were stained with Giemsa and differential counts performed. Single cell suspensions of spleens and PECs were prepared, cell counts performed, CD4+CD62− T-cells were isolated with Miltenyi microbeads and number of cells determined by trypan blue exclusion. For experiments where animals received TAT-mCID or control peptides, 800 μg (40 mg/kg) was injected IP 2 hrs prior to administration of cl-CD95L. All mouse experiments were performed under ethical approval from the University of Nottingham local animal ethics committee and adhering to UK Home Office guidelines under the Project License 40/3412.

Metalloprotease-cleaved and Ig-fused CD95L Production

Ig-CD95L was generated in the laboratory as described in (Tauzin et al., 2011). HEK 293 cells maintained in an 8% FCS-containing medium were transfected using Calcium/Phosphate precipitation method with 3 μg of empty plasmid or wild type CD95L-containing vector. 16 hours after transfection, medium was replaced by OPTI-MEM (Invitrogen) supplemented with 2 mM L-glutamine and 5 days later, media containing cleaved CD95L and exosome-bound full length CD95L were harvested. Dead cells and debris were eliminated through two steps of centrifugation (4500 rpm/15 minutes) and then exosomes were eliminated by an ultra-centrifugation step (100000 g/2 hours).

Size Exclusion Chromatography

Sera from 4 different SLE patients ($5.10^7$ cells) were filtrated using a 0.2 μm filter and then 5 ml was resolved using a mid range fractionation S300-HR Sephacryl column (GE Healthcare) equilibrated with PBS (pH 7.4). Using an AKTAprime purifier apparatus (GE Healthcare), fractions were harvested with a flow rate of 0.5 mL/min. Fifty fractions were harvested and analyzed by ELISA to quantify CD95L.

CD95L ELISA

Anti-CD95L ELISA (Diaclone, Besançon, France) was performed to accurately quantify the cleaved-CD95L present in sera following the manufacturer's recommendations.

Immunoprecipitation

T-cells ($5 \times 10^7$ cells per condition) were stimulated with Ig-CD95L or cl-CD95L (100 ng/mL) for indicated times at 37° C. Cells were lysed, incubated with APO1.3 (1 ug/mL) for 15 min at 4° C. and CD95 was immunoprecipitated using A/G protein-coupled magnetic beads (Ademtech, Pessac, France) for 1 h. After extensive washing, the immune complex was resolved by SDS-PAGE and immunoblotting was performed with indicated antibodies.

Immunoblot Analysis

Cells were lyzed for 30 minutes at 4° C. in lysis buffer (25 mM HEPES pH 7.4, 1% v/v Triton X-100, 150 mM NaCl, 2 mM EGTA supplemented with a mix of protease inhibitors (Sigma-Aldrich)). Protein concentration was determined by the bicinchoninic acid method (PIERCE, Rockford, Ill., USA) according to the manufacturer's protocol. Proteins were separated on a 12% SDS-PAGE and transferred to a nitrocellulose membrane (GE Healthcare, Buckinghamshire, England). The membrane was blocked 15 minutes with TBST (50 mM Tris, 160 mM NaCl, 0.05% v/v Tween 20, pH 7.8) containing 5% w/v dried skimmed milk (TB-STM). Primary antibody was incubated overnight at 4° C. in TBSTM. The membrane was intensively washed (TBST) and then the peroxydase-labeled anti-rabbit or anti-mouse (SouthernBiotech, Birmingham, Ala., US) was added for 45 minutes. The proteins were visualized with the enhanced chemiluminescence substrate kit (ECL, GE Healthcare).

Transendothelial Migration of Activated T Lymphocytes

After hydration of the Boyden chamber membranes containing 3 μm pore size membranes (Millipore, Molsheim, France), activated T-lymphocytes ($10^6$) were added to the top chamber on a confluent monolayer of HUVEC in a low serum (1%)-containing medium. The bottom chamber was filled with low serum (1%)-containing medium in presence or absence of 100 ng/ml of cl-CD95L. In experiments using human sera, 500 μl of serum from either healthy donors or SLE patients was added in the lower reservoir. Cells were cultured for 24 h at 37° C. in a 5% $CO_2$ humidified incubator. Transmigrated cells were counted in the lower reservoir by flow cytometry using a standard of $2.5 \times 10^4$ fluorescent beads (Flow-count, Beckman Coulter).

Endothelial Cell Adhesion Assay

Blocking antibodies were used against E-selectin and ICAM-1 in the CHEMICON® endothelial cell adhesion assay (Millipore). Briefly, after activation of the endothelial cell layer with TNF-α, anti-mouse Ig controls, anti-E-selectin or anti-ICAM-1 were added at final concentrations of 10 μg/ml. Thereafter calcein-AM-stained T-cell subsets were incubated for 24 hours and unbound cells are washed. Cells attached to the endothelium were assessed using fluorescence plate reader.

Real-time qPCR

Single cell suspensions of spleens and PECs were prepared as described above. RNA was extracted from CD4 T-cells using phenol/chloroform. cDNA was prepared using the Promega GO-Script Reverse Transcription Kit and used in Real-Time PCR. Briefly, cDNA samples were subject to Taqman assay performed on a Roche Lightcycler. Results are reported as expression levels were calculated using the Δct method relative to HPRT.

Video Imaging of the Calcium Response in Living Cells

Experiments on Parent Cell Lines

T cells were loaded with Fura-PE3-AM (1 μM) at room temperature for 30 min in Hank's Balanced Salt Solution (HBSS). After washing, the cells were incubated for 15 min in the absence of Fura-PE3-AM to complete de-esterification of the dye. Cells were placed in the temperature controlled chamber (37° C.) of an inverted epifluorescence microscope (Olympus IX70) equipped with an ×40 UApo/ 340-1.15 W water-immersion objective (Olympus), and fluorescence micrograph images were captured at 510 nm and 12-bit resolution by a fast-scan camera (CoolSNAP fx Monochrome, Photometrics). To minimize UV light exposure, a 4×4 binning function was used. Fura-PE3 was alternately excited at 340 and 380 nm, and the ratios of the resulting images (emission filter at 520 nm) were produced at constant intervals (10 seconds). The Fura-PE3 ratio ($F_{ratio}$ 340/380) images were analyzed offline with Universal Imaging software, including Metafluor and Metamorph. $F_{ratio}$ reflects the intracellular $Ca^{2+}$ concentration changes. Each experiment was repeated 3 times, and the average of more than 20 single-cell traces was analyzed.

Experiments on GFP-expressing Cell Lines

Fluo2-AM was used, instead of Fura-PE3-AM for experiments with GFP-expressing cells, because GFP fluorescence disturbs $Ca^{2+}$ measurement with Fura-PE3. As for Fura-PE3-AM, T cells were loaded with Fluo2-AM (1 μM) for 30 min in Hank's Balanced Salt Solution (HBSS) and then incubated for 15 min in the Fluo2-AM free HBSS to complete de-esterification of the dye.$Ca^{2+}$ changes were evaluated by exciting Fluo2-AM-loaded cells at 535±35 nm. The values of the emitted fluorescence (605±50 nm) for each cell (F) were normalized to the starting fluorescence ($F_0$) and reported as $F/F_0$ (relative $Ca^{2+}_{[CYT]}$). Only GFP-positive cells were considered.

Figure 5A:
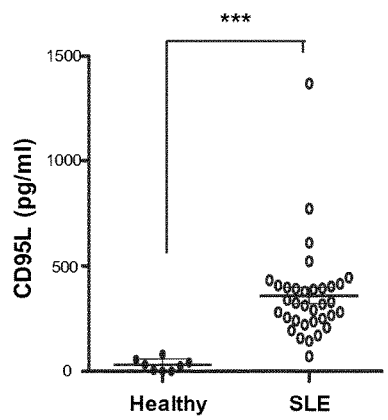
Figure 5B:
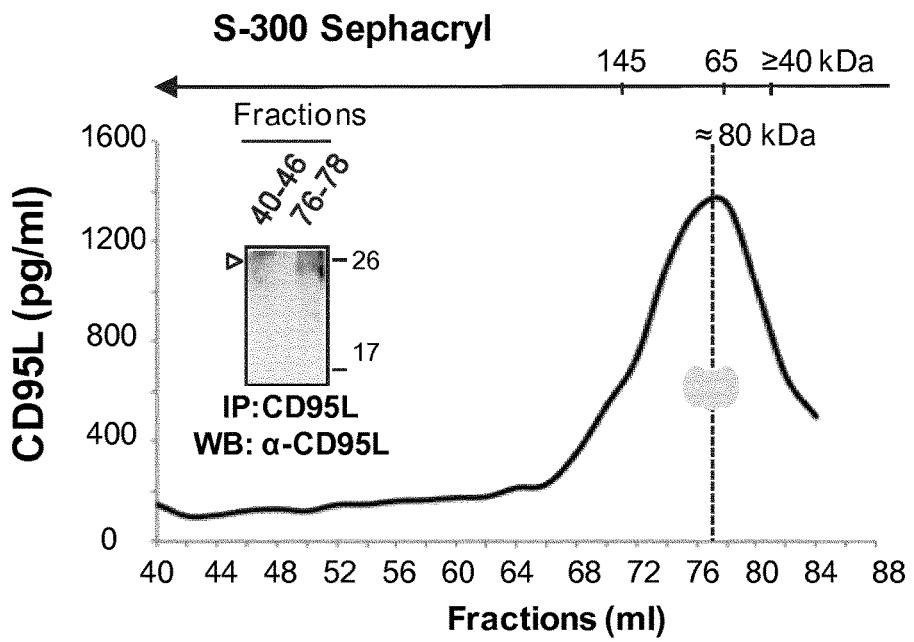
Figure 5C:
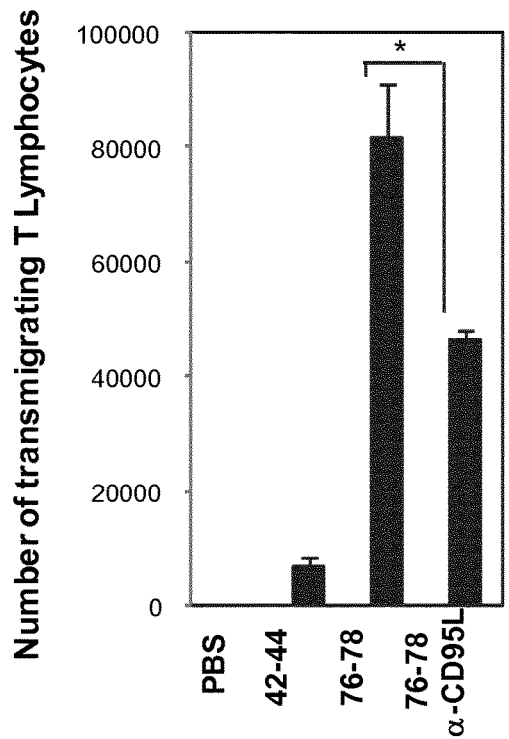
Figure 5D:
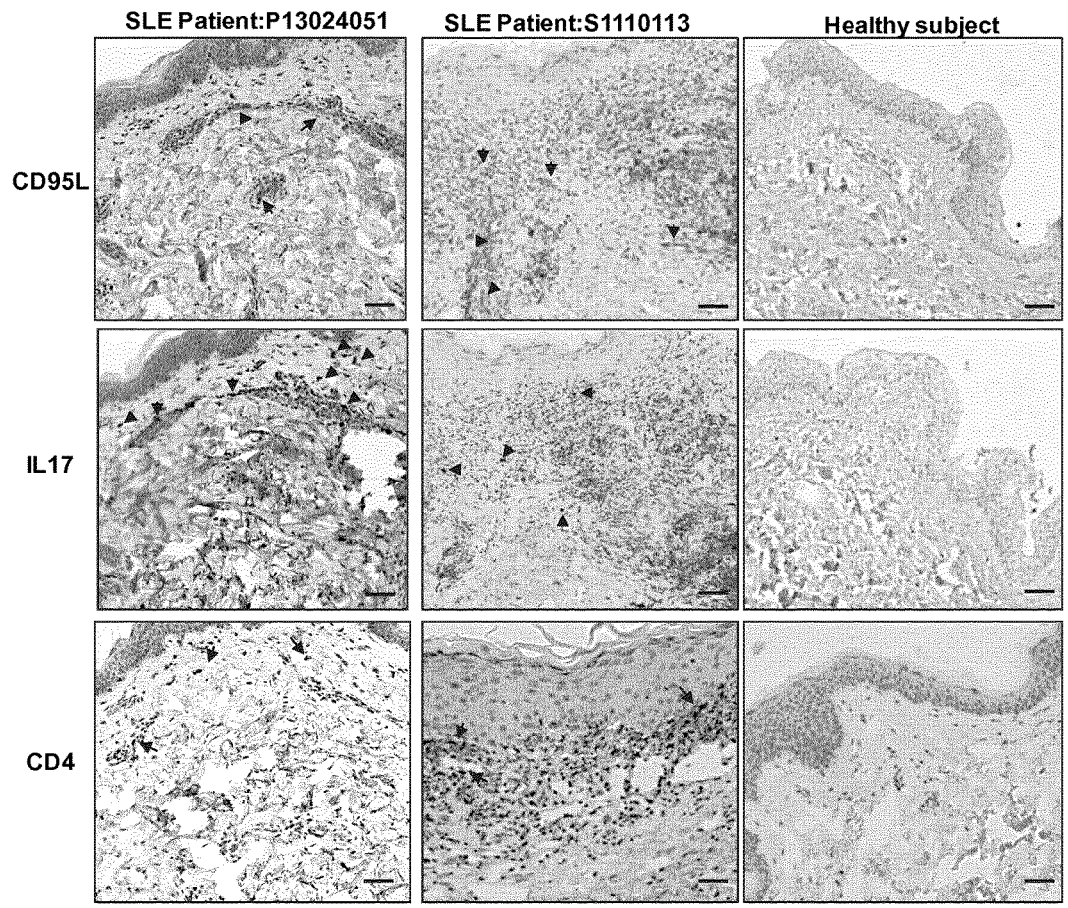
Figure 5E:
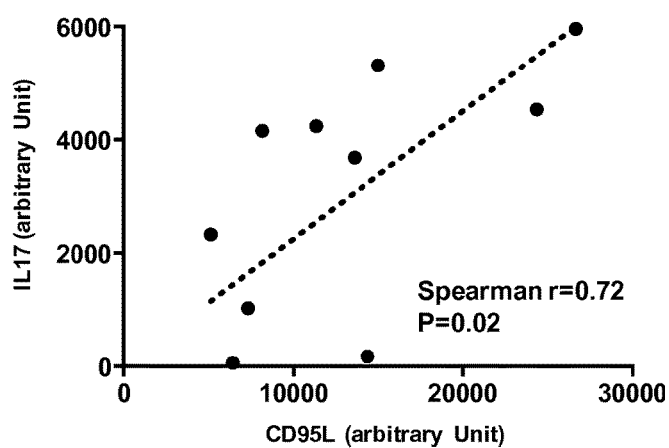
Figure 5F:
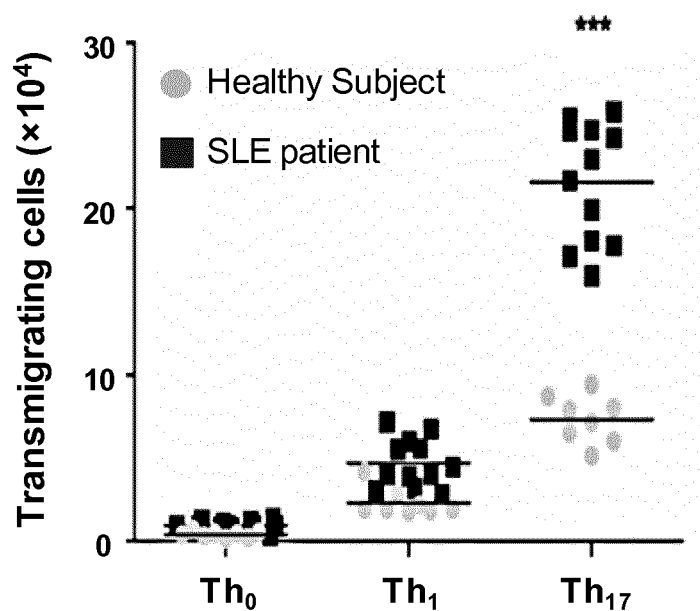
Figure 5G:
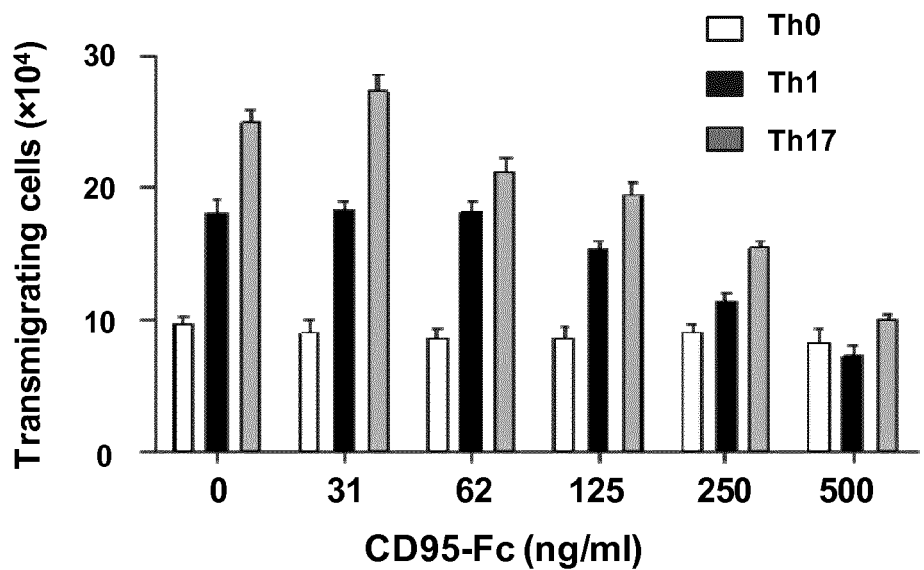

Results:

Serum CD95L in Lupus Patients Promotes Endothelial Transmigration of Activated Th17 Cells Recent reports suggest that a soluble form of CD95L increases in bronchoalveolar lavage fluid of patients suffering from acute respiratory distress syndrome (ARDS). Surprisingly, this soluble CD95L conserves its amino-terminal extracellular stalk region (amino acid residues 103 to 136), a region normally eliminated after shedding by metalloprotease of the membrane-bound CD95L (Herrero et al., 2011). Additionally under native conditions, this ARDS CD95L exhibited a hexameric stoichiometry and exerted a cytotoxic activity towards alveolar epithelial cells in lungs (Herrero et al., 2011). These results encouraged us to evaluate the stoichiometry of serum CD95L in SLE patients. First, we confirmed that soluble CD95L was significantly increased in the sera of 34 SLE patients as compared to 8 age-matched healthy donors (360±224.8 pg/ml in SLE patients vs 30.04±28.52 pg/ml in healthy subjects, P<0.0001) (FIG. 5A). Second, these sera were fractionated using size-exclusion chromatography and CD95L concentration was quantified in each eluted fraction (FIG. 5B). CD95L was detected in fractions 76 to 78, that contained proteins whose native molecular mass ranged between 75 and 80 kDa. This CD95L was next immunoprecipitated and resolved under denaturing/reducing conditions (SDS-PAGE) at 26 kDa (FIG. 5B) indicating that the serum CD95L accumulated in lupus patients corresponded to a homotrimeric ligand. Upon examination, we noted that functionally this serum CD95L retained the previously reported activity of cleaved-CD95L (cl-CD95L), as it promoted the transmigration of T lymphocytes across an endothelial monolayer (FIG. 5C). Specifically, significantly more activated T lymphocytes isolated from healthy donors exposed to fractions 76-78 crossed endothelial monolayers in comparison to lymphocytes exposed to fractions 42-44. These latter fractions, which contain exosome-bound CD95L (data not shown) failed to exert any pro-migratory effect (FIG. 5C). Furthermore, T-cell transmigration induced by fractions 76-78 was inhibited by up to 50% using a neutralizing anti-CD95L mAb (FIG. 5C) confirming that soluble CD95L in SLE patients plays a role in the endothelial transmigration of T lymphocytes. If T-cell infiltration is involved in tissue damage and Th17 cells contribute to this clinical outcome through a CD95-driven recruitment, we assumed that CD95L-expressing cells should be detected in the inflamed organs. Using immunohistochemistry, we evaluated the distribution of CD95L and IL17-expressing cells in lupus patients with skin lesions. Of note, CD95L and IL17 staining were observed in skin biopsies of lupus patients while they were undetectable in control skins (i.e., skins from breast reconstruction) (FIG. 5D). Moreover, CD95L was mainly detected on endothelium of blood vessels, which were surrounded by immune cell infiltration (FIG. 5D). Moreover, a densitometric analysis of lupus patients (n=10) highlighted that the amount of CD95L was correlated with the quantity of tissue-infiltrating IL17-expressing immune cells suggesting that this ligand may represent a chemoattractant for $CD4^+$ Th17 cells (FIG. 5E). To further investigate if after cleavage by metalloprotease, CD95L exerted a chemoattractant activity toward all T-lymphocytes or selectively promoted migration of a sub-population, endothelial transmigration of naïve $CD4^+$ T-cells isolated from healthy donors and subjected to in vitro differentiation was evaluated in presence or absence of healthy or SLE sera. As compared to healthy sera, sera from SLE patients triggered a moderate increase in Th1 transmigration while they dramatically enhanced endothelial transmigration of Th17 cells (FIG. 5F). More importantly, this transmigration process relied on CD95 signaling because pre-incubation of SLE sera with a decoy receptor (CD95-Fc) prevented Th17 cell migration in a dose-dependent manner (FIG. 5G).

Figure 5H:
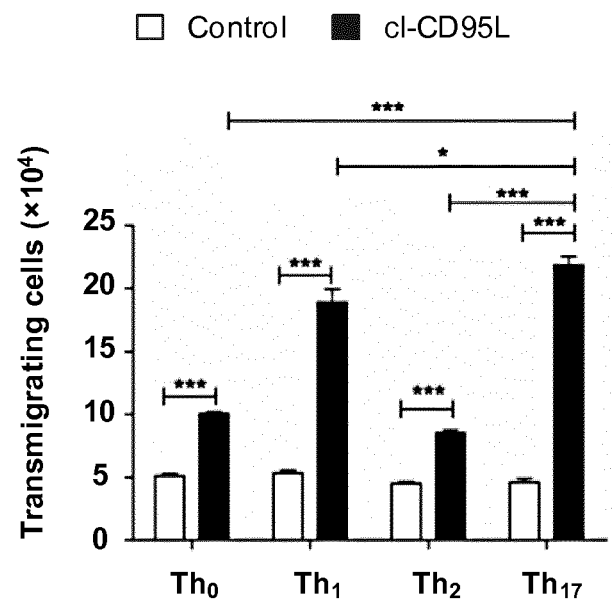
Figure 5I:
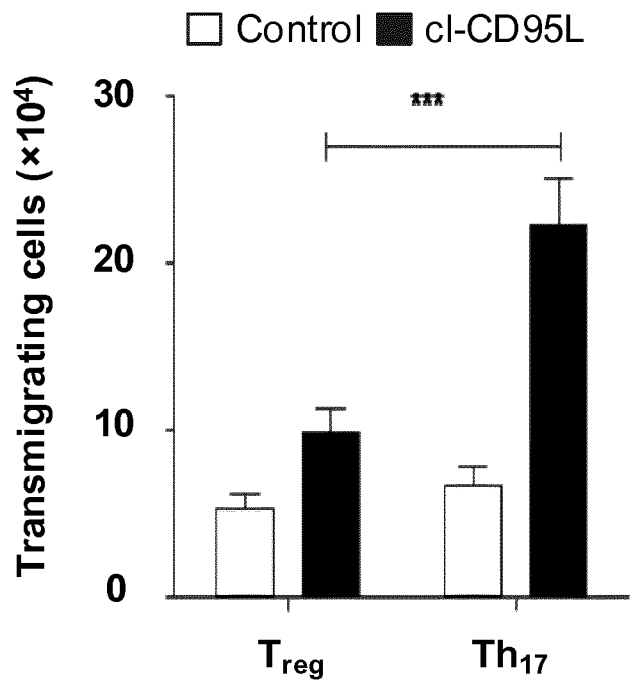

Both Th1 and Th17 T-cells have been reported to accumulate in enflamed organs of lupus patients and lupus-prone mice contributing to disease pathogenesis. To eliminate a putative role played by other serum components in the observed phenomenon, we hereafter used a recombinant and homotrimeric version of CD95L. To this end, HEK 293 cells were transfected with a full-length CD95L-encoding vector and we used the metalloprotease-cleaved CD95L (cl-CD95L) contained in this supernatant (Tauzin et al., 2011). Similarly to serum CD95L in lupus patients, cl-CD95L was more efficient to promote the transmigration of Th1 and Th17 lymphocytes as compared to undifferentiated Th0 and differentiated Th2 cells (FIG. 5H). As imbalance of the Th17/T-regulatory (Treg) cell ratio in enflamed organs has been suggested to participate in autoimmune disorders and specifically lupus pathogenesis (Yang et al., 2009), we next evaluated the effect of cl-CD95L on the transmigration of Treg cells. As shown in FIG. 5I, cl-CD95L enhanced endothelial transmigration of Th17 T cells but failed to induce significant Treg transmigration indicating that the accumulation of Th17 cells at the expense of Treg cells in the inflamed tissues of lupus patients. These findings revealed that the higher levels of serum CD95L in SLE patients as compared to healthy donors could contribute to the accumulation of Th17 cells in inflamed organs.

Cellular recruitment and trafficking can be controlled by expression levels of adhesion molecules on lymphocytes and their molecular partners on endothelial cell surfaces. The expression of these molecules during an inflammatory response is a dynamic process, which increases or decreases the extravasation of immune cells into tissues. Recently, Th17 cells have been shown to accumulate in organs as a result of their interaction with E-selectin during rolling and ICAM-1-dependent arrest on activated endothelium (Alcaide et al., 2012). To address if these molecules contributed to the CD95-mediated endothelial T-cell migration of Th17 cells, we evaluated the expression level of key adhesion molecules on endothelial cells and differentiated Th cells in presence or absence of cl-CD95L. Of note, while an important amount of E-selectin was observed at the surface of HUVECs, no P-selectin was detected in these cells. Moreover, cl-CD95L did not alter the expression level of different adhesion molecules on HUVEC. By contrast, in presence of cl-CD95L, Th17 cells underwent up-regulation of P-selectin glycoprotein (PSGL-1), a ligand of E- and P-selectin, and ICAM-1 binding partner LFA-1. The expression level of these ligands remained unaffected in Th1 cells and tended towards a down-regulated state in Treg cells. Functionally the impact of PSGL-1 up-regulation in cl-CD95L-stimulated Th17 cells was evaluated by use of an E-selectin neutralizing mAb. Anti-E-selectin inhibited more efficiently Th17 cell transmigration when compared to similarly treated Th1 cells. Conversely blockade of ICAM-1/LFA-1 interactions by anti-ICAM-1 mAb impaired to a lesser extent both Th1 and Th17 cell migration across endothelial cells. These findings suggested that cl-CD95L promoted CD95-mediated Th17 cell transmigration by enhancing PSGL-1/E-selectin interaction.

Cl-CD95L Causes In Vivo a Rapid Accumulation of Th17 Cells.

To confirm in vivo the chemoattractant ability of cl-CD95L towards Th17 cells, mice were injected intraperitoneally with a single dose of cl-CD95L or vehicle and 24 hours later, composition of T-cells infiltrating the peritoneal cavity (peritoneal exudate cells—PECs) and the spleen was examined. Total cell counts from the PEC and spleen revealed a significant increase in the number of lymphocytes in these compartments as compared to vehicle-injected mice (FIG. 6A-B). Loss of CD62L expression is associated with T-cell receptor engagement. Using this marker, we evaluated the amount of activated $CD4^+$ T-cells ($CD4^+CD62L^-$) recruited into the spleen and the peritoneal cavity of mice injected with or without cl-CD95L. We observed an increased amount of T cells recruited in the peritoneal cavity and the spleen upon injection of cl-CD95L as compared to control medium (FIG. 6C-D). Moreover, Q-PCR analyses of key markers of the Th17 lineage including IL-17 (FIG. 6E), IL-23R (FIG. 6F), and CCR6 (FIG. 6G), performed on these activated CD4+ T cells showed that cl-CD95L induced the recruitment of Th17 cells in these tissues. Furthermore, there was no increase in levels of IFN-γ (Th1 cells) and FoxP3 (Treg) levels upon examination (FIG. 6H-I) strongly supporting that cl-CD95L acted primarily as a potent chemotactic ligand to Th17 T cells.

CD95 Triggers a Death Domain-Independent Ca' Response

Figure 7A:
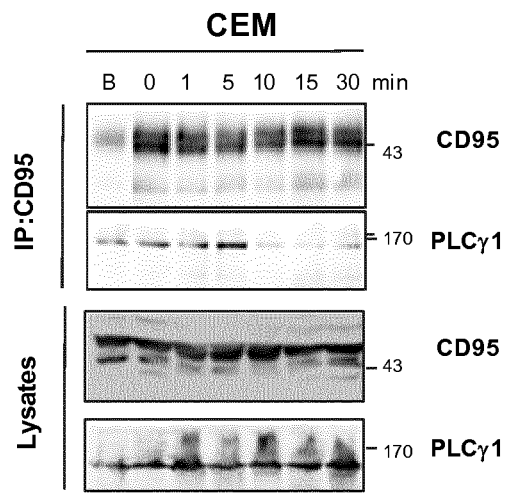
Figure 7B:
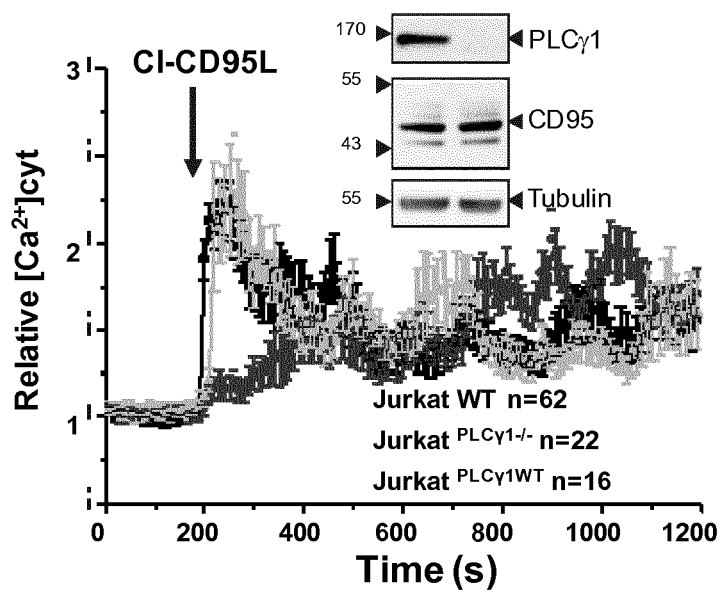
Figure 7C:
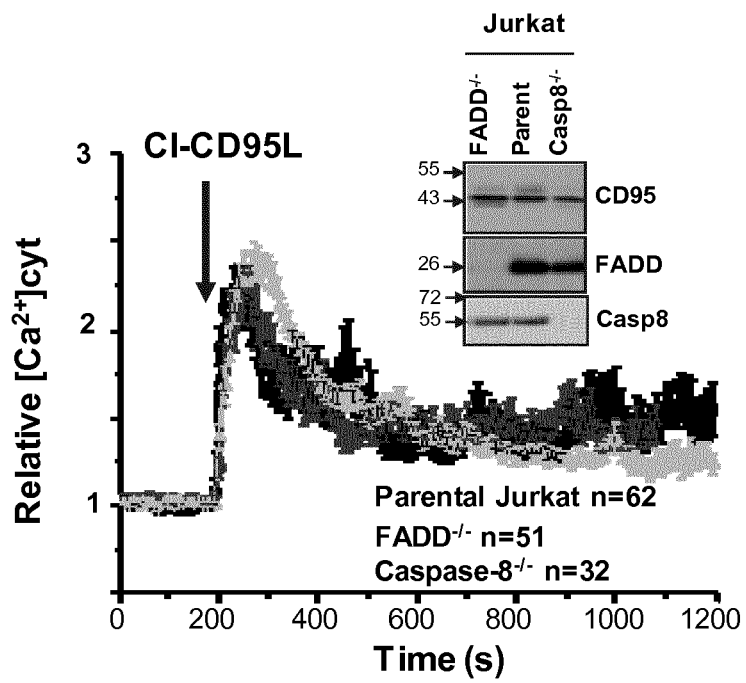
Figure 7D:
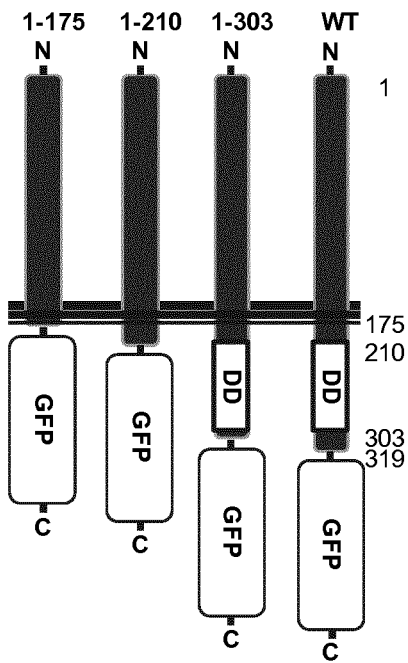
Figure 7E:
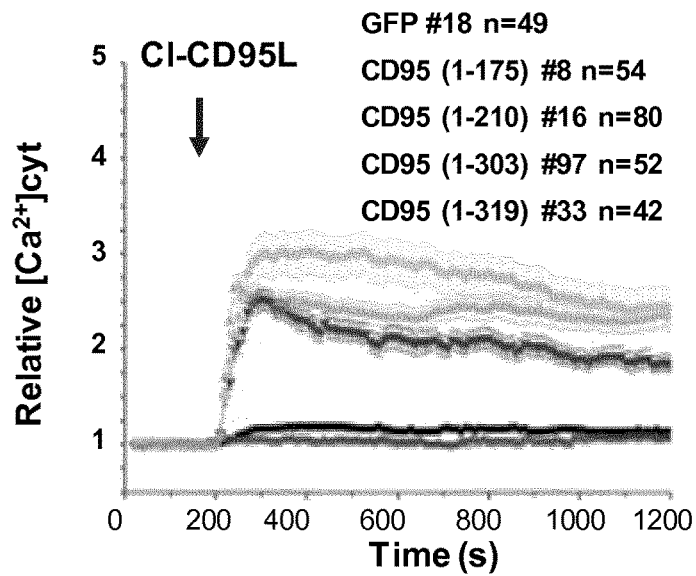
Figure 8A:
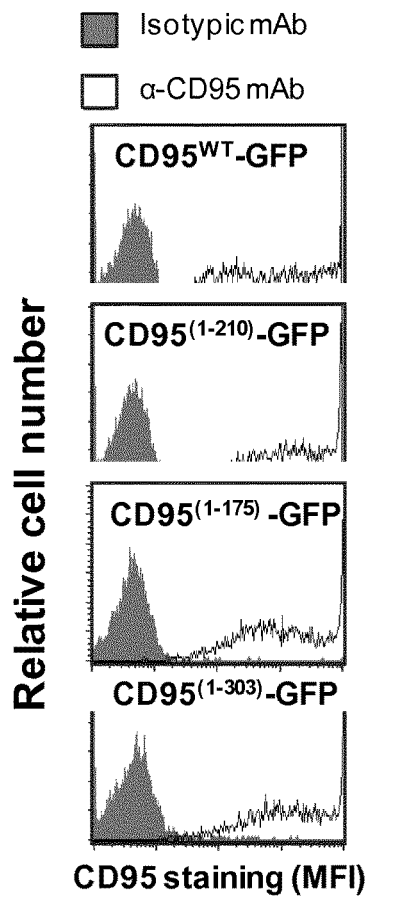
Figure 8B:
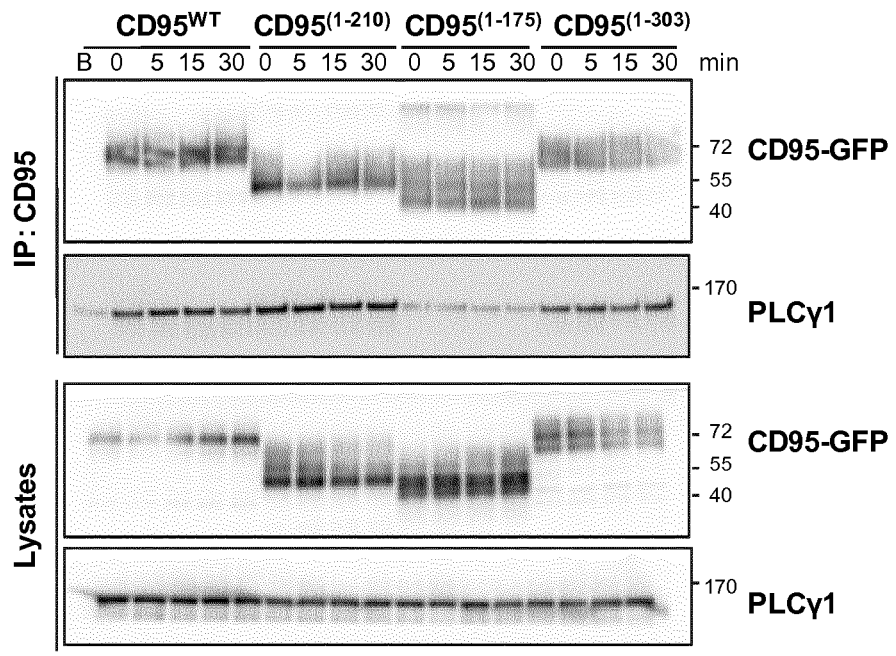
Figure 8C:
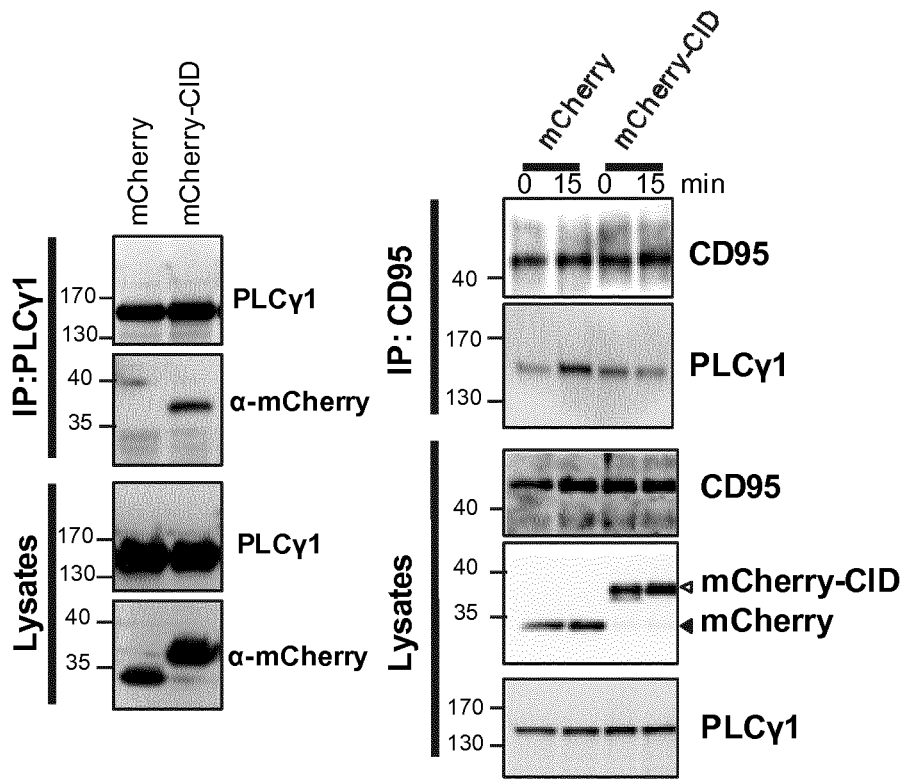
Figure 8D:
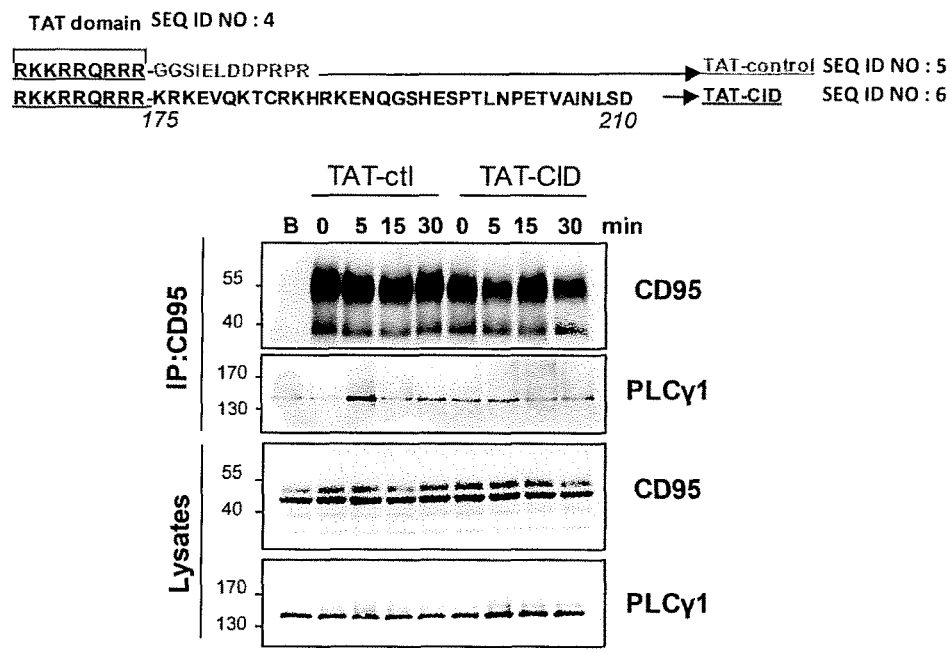
Figure 8E:
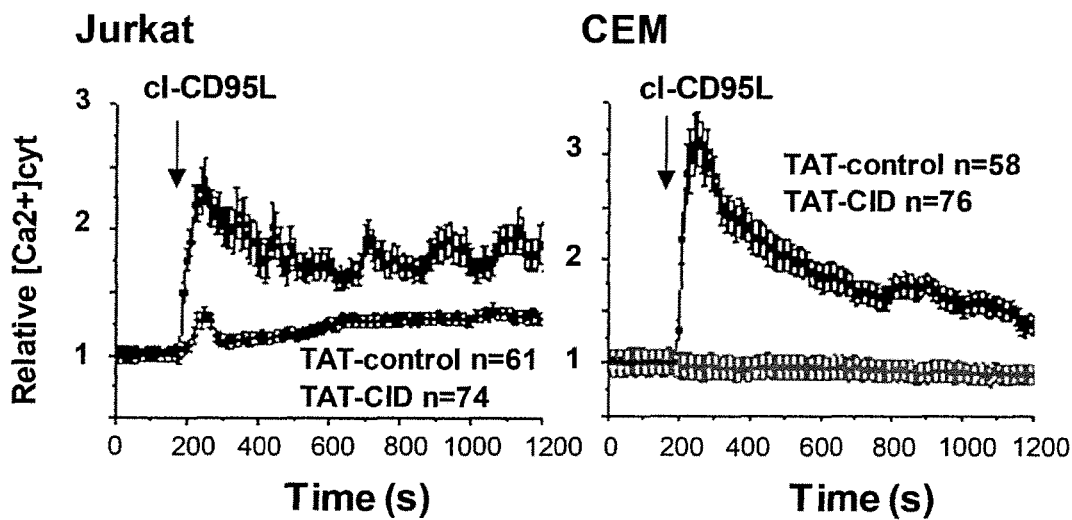
Figure 8F:
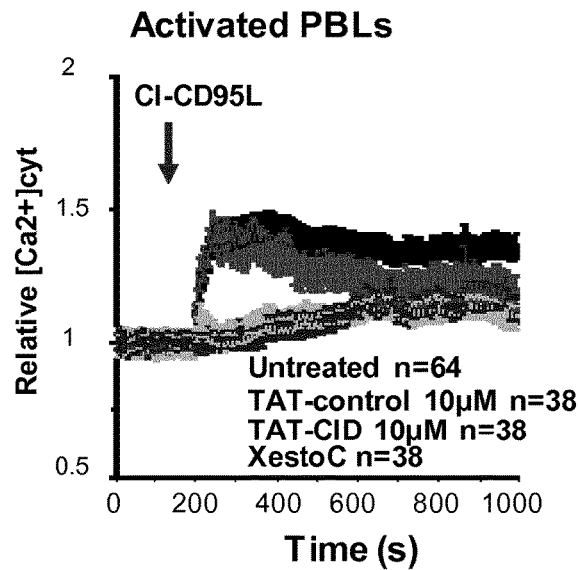

We recently showed that CD95 engagement evoked a $Ca^{2+}$ response in activated T lymphocytes that transiently inhibited the apoptotic signal (Khadra et al., 2011) and promoted cell motility (Tauzin et al., 2011). These observations raised the question of whether inhibition of this CD95-mediated $Ca^{2+}$ response can simultaneously inhibit cell migration and enhance or at least unalter the apoptotic signal. T-cells exposed to cl-CD95L rapidly formed a molecular complex containing the phospholipase Cγ1 (PLCγ1) (FIG. 7A). Of note, the lack of this lipase in the T-cell line Jurkat caused a loss of the CD95-mediated $Ca^{2+}$ signal, while reconstitution of these cells with wild type PLCγ1 restored a calcium response similar to that of the parental T-cell line (FIG. 7B). Next, we investigated if the main components of the DISC were instrumental in the CD95-mediated calcium signal. To this end, the calcium signal was assessed in FADD- and caspase-8-deficient Jurkat cells stimulated with cl-CD95L (FIG. 7C). Interestingly, although elimination of these molecules blocked the transmission of the apoptotic signaling pathway, it did not affect the CD95-mediated $Ca^{2+}$ signal (FIG. 7C) indicating that PLCγ1 activation occurred independently of the DISC formation and the implementation of cell death signal. These data prompted us to analyze if the CD95-DD itself was necessary to trigger the $Ca^{2+}$ response. CD95 constructs devoid of either the entire intracellular domain ($CD95^{1-175}$), the DD ($CD95^{1-210}$) or only the last 15 amino acids involved in the FAP-1 recruitment ($CD95^{1-303}$) were generated (FIG. 7D). Protein-tyrosine phosphatase FAP-1 is reported to interact with the carboxyl terminal 15 amino acids of CD95 (Sato et al., 1995) and prevent its export from the cytoplasm to the cell surface (Ivanov et al., 2003). These constructs were expressed in a T-cell line selected for its low expression level of CD95 namely CEM-IRC ((Beneteau et al., 2008). While CEM-IRC cells showed a trivial sensitivity to cytotoxic CD95L, expression of $CD95^{1-303}$ or wild type CD95 in CEM-IRC cells to a level similar to that of endogenous CD95 in parental CEM cells restored the transmission of the apoptotic signaling pathway. By contrast, high levels of $CD95^{1-175}$ or $CD95^{1-210}$ failed to induce cell death and as previously observed behave as dominant-negative receptors (Siegel et al., 2000). Also, reconstitution of CEM-IRC cells with wild type CD95 and $CD95^{1-303}$ restored the CD95-mediated $Ca^{2+}$ signal (FIG. 7E). Strikingly, while the loss of the death domain in the $CD95^{1-210}$ construct prevented the implementation of the apoptotic signal, it did not affect the induction of the $Ca^{2+}$ signal (FIG. 7E). Given that a CD95 construct devoid of its whole intracellular region failed to evoke a $Ca^{+2}$ response, we concluded that the $Ca^{2+}$ response stems from the first 36 amino acids in the CD95 intracellular region. To confirm that amino acid residues 175 to 210 of CD95 were responsible for the $Ca^{2+}$ response, we determined if this domain was capable to interact with PLCγ1. To this end, GFP-fused CD95 constructs and wild type PLCγ1 were first transiently transfected in HEK cells, cells were stimulated with CD95L, lyzed and the immune complex associated with CD95 was analyzed by immunoblotting. Although cells expressed similar levels of the different CD95 chimeric constructs (FIG. 8A), the presence of PLCγ1 in the CD95 immunoprecipitate was only lost with the $CD95^{1-175}$ construct (FIG. 8B), while both $CD95^{1-210}$ and $CD95^{1-175}$ lost their capacity to recruit the adaptor protein FADD. Interestingly, a CD95 construct devoid of DD showed a higher binding capacity for PLCγ1 as compared to wild type CD95 (FIG. 8B) suggesting that this region may structurally or functionally interfere with the PLCγ1 binding to the 175-210 domain. Second, we generated a construct consisting of amino acids 175 to 210 that we designated calcium-inducing domain (CID) fused to mCherry. Unlike mCherry alone, $CD95^{(175-210)}$-mCherry interacted with PLCγ1 and inhibited its recruitment to CD95 (FIG. 8C) indicating that interference with this juxtamembrane domain may represent a way to prevent the CD95-mediated $Ca^{2+}$ signal. Finally, to confirm this hypothesis, we synthesized a cell penetrating peptide linking the 36-amino acid-stretch of CID to the 9-amino acid HIV-TAT sequence (FIG. 8D), which serves as carrier to translocate the whole protein across plasma membrane (Vives et al., 1997). Pre-incubation of the T cell lines Jurkat and CEM with the TAT-CID peptide impaired PLCγ1 recruitment (FIG. 8D) and abolished the induction of the CD95-mediated $Ca^{2+}$ signal (FIG. 8E). Similarly, pre-incubation of activated T lymphocytes from healthy subjects with the TAT-CID inhibited the PLCγ1 binding to CD95 (FIG. 54A) and abrogated the CD95-mediated $Ca^{2+}$ response, in a similar way to xestospongin C, an antagonist of the calcium-releasing action of inositol-1,4,5-trisphosphate (IP3), the substrate generated by PLCγ1 activation (FIG. 8F). Moreover, TAT-CID pre-incubation inhibited Akt phosphorylation at its serine 473 (a hallmark of the PI3K signaling pathway activation) in PBLs exposed to cl-CD95L. Of note, although TAT-CID treatment inhibited the CD95-mediated $Ca^{2+}$ and PI3K signals, it did not affect the execution of the apoptotic signaling pathway. In conclusion, we mapped a novel domain in CD95 designated calcium-initiating domain that recruited PLCγ1 and elicited the $Ca^{2+}$ response.

Because cysteine at position 183 is subject to palmitoylation promoting CD95 aggregation (Feig et al., 2007) and its redistribution into lipid raft (Chakrabandhu et al., 2007), we wondered whether this amino acid was instrumental in the implementation of the CD95-mediated $Ca^{2+}$ signal. To address this question and yet avoid any interference of the apoptotic signaling in the CD95-mediated $Ca^{2+}$ response, we reconstituted CEM-IRC cells with a $CD95^{1-210}$ (no death domain) in which cysteine 183 was replaced by a valine. Both $CD95^{1-210}$ and $CD95^{1-210(C183V)}$ failed to trigger cell death in presence of Ig-CD95L, but they evoked a similar $Ca^{2+}$ response suggesting that the mechanism of palmitoylation was not instrumental in inducing this cue. To confirm this observation, a TAT-CID peptide was synthesized in which cysteine was replaced by a valine. Pre-incubation of Jurkat cells and activated PBLs with this mutated peptide still inhibited the CD95-mediated $Ca^{2+}$ response confirming that this cysteine did not contribute to the $Ca^{2+}$ response in cells exposed to cl-CD95L. Finally, we evaluated if the inhibitory effect of the TAT-CID was selective of the CD95-mediated $Ca^{2+}$ signal. Of note, although TCR stimulation led to a PLCγ1-dependent $Ca^{2+}$ response, TAT-CID pretreatment did not alter this signal. Similarly, the PLCβ-driven $Ca^{2+}$ response evoked by carbachol, a cholinergic agonist known to evoke a $Ca^{2+}$ response through activation of G-protein-coupled receptors, was not affected by TAT-CID treatment. These findings indicated that the TAT-CID peptide exerted a selective inhibition of the CD95-mediated calcium signal.

Inhibition of the CD95-mediated $Ca^{2+}$ Signal Prevents Th17 Cell Transmigration and Alleviates Clinical Signs in Lpr Mice.

To address if TAT-CID regimen may represent a therapeutic strategy in lupus, we first evaluated its effect in Th17 cell transmigration. As shown in FIG. 9A, TAT-CID inhibited the CD95-mediated endothelial transmigration of human Th17 cells in a dose-dependent manner. Alignment of human and mouse CD95 proteins indicated a sequence divergence in the CID region suggesting that the human CID (TAT-hCID) may turn out to be inefficient to prevent the $Ca^{2+}$ response induced in mouse T cells. To determine the inhibitory activity of TAT-hCID on the $Ca^{2+}$ response induced by murin CD95, we first reconstituted CEM-IRC cells with wild type mouse CD95. Both CD95-mediated apoptotic and $Ca^{2+}$ signals were restored in these cells as compared to parental CEM-IRC cells. Importantly, TAT-hCID failed to inhibit the CD95-mediated $Ca^{2+}$ response in mouse CD95-expressing CEM-IRC cells. By contrast, replacement of the human CID sequence by its mouse ortholog (TAT-mCID) abolished the CD95-mediated $Ca^{2+}$ response in these cells. Similarly, TAT-mCID also inhibited the CD95-mediated $Ca^{2+}$ signal in mouse T lymphocytes confirming that despite the divergence between human and mouse CD95-CID sequences (48.9% of sequence identity over the complete human and mouse CD95 sequences vs 21.2% over the two CIDs), these domains retained the property to trigger the $Ca^{2+}$ signal in these species.

To further investigate the putative therapeutic activity of TAT-CID and determine whether this peptide exerted an inhibitory effect on Th17 T-cell recruitment in vivo, we injected C57Bl/6 mice with 40 mg/kg of TAT-control or TAT-CID two hours prior to the intraperitoneal injection of cl-CD95L and the amount of T-cells infiltrating the peritoneal cavity was evaluated 24 hours later. Total cell counts from the PEC revealed that TAT-CID regimen abolished the CD95-mediated accumulation of T lymphocytes in this compartment (FIG. 9B). In agreement with data shown in FIG. 2, cl-CD95L injection triggered an increased IL17 production in the peritoneal cavity that was prevented by the TAT-CID treatment (FIG. 9C). Furthermore, no differences were noted in levels of IFN-γ between mice injected with control peptide and TAT-CID peptide highlighting that the preferential recruitment of IL-17 secreting CD4 T-cells by cl-CD95L was abolished in vivo by administration of TAT-CID.

In conclusion, the selective inhibition of the CD95-mediated $Ca^{2+}$ signal turned out to be a novel and promising therapeutic strategy to reduce Th17 cell accumulation in inflamed tissues of lupus patient without altering the transmission of the apoptotic signal.

Discussion:

Our study provides new insights into the cellular and molecular mechanisms by which metalloprotease-cleaved CD95L enhances inflammation in SLE patients. We show that transmembrane CD95L is ectopically expressed by endothelial cells covering blood vessels in the inflamed skins of lupus patients. More importantly, these $CD95L^+$ vessels are surrounded by a massive immune infiltrate strongly suggesting that these structures may serve as "open doors" for pro-inflammatory cells among which Th17 cells. Exposed to cl-CD95L, these IL17-expressing cells up-regulate PSGL-1 and LFA-1, two adhesion molecules involved in rolling and tethering of leukocytes to endothelial cells. Of note, T cells with the highest levels of functional PSGL-1 also show the greatest capacity for effector cytokine secretion and for cytotoxic activity (Baaten et al., 2013). Therefore, cl-CD95L may fuel the inflammatory process not only by promoting the recruitment of activated Th1 and Th17 cells in inflamed tissues but also by altering the pattern of cytokine release in these organs.

Recently, Coukos and colleagues demonstrated that CD95L is present in blood vessels of certain cancer tissues (i.e., ovary, colon, prostate, kidney) (Motz et al., 2014) and they associated this staining with scarce $CD8^+$ infiltration. These authors showed that membrane-bound CD95L on endothelial cells eliminated T cells and by doing so, prevented effective anti-tumor immunity (Motz et al., 2014). We evaluated the $CD8^+$ T-cell infiltration around CD95L-positive blood vessels in lupus patients and densitometric analysis revealed no inverted correlation between the amounts of CD95L and the quantity of infiltrating $CD8^+$ T cells. Given that CD95L exerts its chemottractant activity only after its cleavage by metalloproteases (Tauzin et al., 2011), we assume that at least in part, the discrepancy in the magnitude of immune infiltrates surrounding $CD95^+$-blood vessels observed in certain cancers and lupus patients may be caused by the absence or the presence, respectively of a CD95L-processing metalloprotease that remains to be identified.

Our study also uncovers the CD95 residues involved in the implementation of the $Ca^{2+}$ signaling pathway. Even if our data show that CID interacts with PLCγ1 in unstimulated cells (FIG. 8C) suggesting that a direct interaction may occur between CD95 and this lipase, we can not rule out that a third partner participates in this association. For example, a recent study showed that TRIP6 over-expressed in glioblastoma links the CID domain to the NF-kB signaling pathway and thereby promotes CD95-mediated cell migration in these cells (Lai et al., 2010). Nonetheless, the same authors did not detect TRIP6 in Jurkat T-cells and precluded its participation in the non-apoptotic signal triggered in T cells suggesting a tissue specific activity of this molecule (Lai et al., 2010). Within neuronal cells, the juxtamembrane domain of CD95 (amino acid residues 175 to 188) interacts with ezrin an adaptor molecule linking CD95 to the actin network and thereby promotes neurite outgrowth via Rac1 activation and cytoskeletal remodeling (Desbarats et al., 2003). Cl-CD95L induces PLCγ1 recruitment rapidly (in the order of the minute) and transiently. Given that this signal stems from CID, this juxtamembrane domain of CD95 will require further analysis of its structure activity relationship to understand how it can evoke the $Ca^{2+}$ response without implementing the death domain-dependent and caspase-driven apoptotic signaling pathway.

In this regard, the 175-210 amino acid residues of CD95 involved in the execution of the $Ca^{2+}$ response has never been crystallized probably due to the fact that this region corresponds to an intrinsically disordered region (IDR) lacking a unique three dimensional structure. Using different molecular dynamic experiments, we confirmed that this peptide has a very faint folding propensity. Computer simulation also showed that the peptide shares another property of IDR: switches between order and disorder states are frequent. Therefore, we surmise that the peptide (or a part of it) may stably fold in the presence of binding partners, starting from a pre-structured region such as helical segments observed by atomistic simulations (Sugase K. et al., Nature, 447, 1021-1025, 2007; Wright & Dyson, Curr. Opin. Struct. Biol., 19, 31-38, 2009). Significantly, IDRs in proteins tend to take a central role in protein interaction networks (Cumberworth et al., 2013). Indeed, these disordered regions can transiently interact with a large number of partners and thereby modulate cell signaling in a dynamic manner. This molecular feature is consistent with the participation of this domain in inducing a rapid and transient $Ca^{2+}$ response promoting cell migration.

Also an analysis of mutations within CD95 found in different pathologies revealed that this region exhibits a lower amount of mutations as compared to the adjacent death domain suggesting that in contrast to the DD, accumulation of mutations in this region may not confer a selective advantage in carcinogenesis or contribute to the inflammatory process in ALPS patients. Of note, before the etiology of ALPS type Ia was associated with mutations in CD95 gene, these patients were erroneously diagnosed as SLE patients.

A recent Phase I/II clinical trial found that a decoy receptor (known as APG101) capable of blocking the CD95/CD95L interaction did not show any toxicity in humans suffering from glioblastoma (Tuettenberg et al., 2012). We may envision that this therapeutic agent may, in a short-term period, benefit lupus patients. However, given that this inhibitor does not discriminate between the anti-tumor/infective functions of CD95L (i.e., the apoptotic signal) and its pro-inflammatory activity, it may leads to deleterious side effects precluding its use in these SLE patients. Because the apoptotic and the calcium signals stem from two separate and distant domains in CD95 and that inhibition of the CD95-mediated $Ca^{2+}$ response does not prevent the apoptotic signaling pathway (Khadra et al., 2011), we propose that selective inhibition of the CD95-mediated $Ca^{2+}$ response will provide an excellent opportunity to block the pro-inflammatory activity of cl-CD95L in certain chronic inflammatory disorders without affecting the anti-tumor and infectious roles of its membrane-bound counterpart.

REFERENCES

Throughout this application, various references describe the state of the art to which this invention pertains. The disclosures of these references are hereby incorporated by reference into the present disclosure.

Alcaide, P., E. Maganto-Garcia, G. Newton, R. Travers, K. J. Croce, D. X. Bu, F. W. Luscinskas, and A. H. Lichtman. 2012. Difference in Th1 and Th17 lymphocyte adhesion to endothelium. J Immunol 188: 1421-1430.

Baaten, B. J., A. M. Cooper, S. L. Swain, and L. M. Bradley. 2013. Location, Location, Location: The Impact of Migratory Heterogeneity on T Cell Function. Frontiers in immunology 4:311.

Beneteau, M., S. Daburon, J. F. Moreau, J. L. Taupin, and P. Legembre. 2007. Dominant-negative Fas mutation is reversed by down-expression of c-FLIP. Cancer Res 67:108-115.

Beneteau, M., M. Pizon, B. Chaigne-Delalande, S. Daburon, P. Moreau, F. De Giorgi, F. Ichas, A. Rebillard, M. T. Dimanche-Boitrel, J. L. Taupin, J. F. Moreau, and P. Legembre. 2008. Localization of Fas/CD95 into the lipid rafts on down-modulation of the phosphatidylinositol 3-kinase signaling pathway. Mol Cancer Res 6:604-613.

Chakrabandhu, K., Z. Herincs, S. Huault, B. Dost, L. Peng, F. Conchonaud, D. Marguet, H. T. He, and A. O. Hueber. 2007. Palmitoylation is required for efficient Fas cell death signaling. Embo J 26:209-220.

Crispin, J. C., M. Oukka, G. Bayliss, R. A. Cohen, C. A. Van Beek, I. E. Stillman, V. C. Kyttaris, Y. T. Juang, and G. C. Tsokos. 2008. Expanded double negative T cells in patients with systemic lupus erythematosus produce IL-17 and infiltrate the kidneys. J Immunol 181:8761-8766.

Cumberworth, A., G. Lamour, M. M. Babu, and J. Gsponer. 2013. Promiscuity as a functional trait: intrinsically disordered regions as central players of interactomes. Biochem J 454:361-369.

Desbarats, J., R. B. Birge, M. Mimouni-Rongy, D. E. Weinstein, J. S. Palerme, and M. K. Newell. 2003. Fas engagement induces neurite growth through ERK activation and p35 upregulation. Nat Cell Biol 5:118-125.

Feig, C., V. Tchikov, S. Schutze, and M. E. Peter. 2007. Palmitoylation of CD95 facilitates formation of SDS-stable receptor aggregates that initiate apoptosis signaling. Embo J 26:221-231.

Fouque, A., L. Debure, and P. Legembre. 2014. The CD95/CD95L signaling pathway: A role in carcinogenesis. Biochim Biophys Acta Herrero, R., O. Kajikawa, G. Matute-Bello, Y. Wang, N. Hagimoto, S. Mongovin, V. Wong, D. R. Park, N. Brot, J. W. Heinecke, H. Rosen, R. B. Goodman, X. Fu, and T. R. Martin. 2011. The biological activity of FasL in human and mouse lungs is determined by the structure of its stalk region. The Journal of clinical investigation 121:1174-1190.

Ivanov, V. N., P. Lopez Bergami, G. Maulit, T. A. Sato, D. Sassoon, and Z. Ronai. 2003. FAP-1 association with Fas (Apo-1) inhibits Fas expression on the cell surface. Mol Cell Biol 23:3623-3635.

Jaffe, E. A., R. L. Nachman, C. G. Becker, and C. R. Minick. 1973. Culture of human endothelial cells derived from umbilical veins. Identification by morphologic and immunologic criteria. J Clin Invest 52:2745-2756.

Khadra, N., L. Bresson-Bepoldin, A. Penna, B. Chaigne-Delalande, B. Segui, T. Levade, A. M. Vacher, J. Reiffers, T. Ducret, J. F. Moreau, M. D. Cahalan, P. Vacher, and P. Legembre. 2011. CD95 triggers Orai1-mediated localized Ca2+ entry, regulates recruitment of protein kinase C (PKC) beta2, and prevents death-inducing signaling complex formation. Proc Natl Acad Sci USA 108:19072-19077.

Kiaei, M., K. Kipiani, N. Y. Calingasan, E. Wille, J. Chen, B. Heissig, S. Rafii, S. Lorenzl, and M. F. Beal. 2007. Matrix metalloproteinase-9 regulates TNF-alpha and FasL expression in neuronal, glial cells and its absence extends life in a transgenic mouse model of amyotrophic lateral sclerosis. Exp Neurol 205:74-81.

Kirkin, V., N. Cahuzac, F. Guardiola-Serrano, S. Huault, K. Luckerath, E. Friedmann, N. Novac, W. S. Wels, B. Martoglio, A. O. Hueber, and M. Zornig. 2007. The Fas ligand intracellular domain is released by ADAM10 and SPPL2a cleavage in T-cells. Cell Death Differ 14:1678-1687.

Kischkel, F. C., S. Hellbardt, I. Behrmann, M. Germer, M. Pawlita, P. H. Krammer, and M. E. Peter. 1995. Cytotoxicity-dependent APO-1 (Fas/CD95)-associated proteins form a death-inducing signaling complex (DISC) with the receptor. Embo J 14:5579-5588.

Kleber, S., I. Sancho-Martinez, B. Wiestler, A. Beisel, C. Gieffers, O. Hill, M. Thiemann, W. Mueller, J. Sykora, A. Kuhn, N. Schreglmann, E. Letellier, C. Zuliani, S. Klussmann, M. Teodorczyk, H. J. Grone, T. M. Ganten, H. Sultmann, J. Tuttenberg, A. von Deimling, A. Regnier-Vigouroux, C. Herold-Mende, and A. Martin-Villalba. 2008. Yes and PI3K bind CD95 to signal invasion of glioblastoma. Cancer Cell 13:235-248.

Lai, Y. J., V. T. Lin, Y. Zheng, E. N. Benveniste, and F. T. Lin. 2010. The adaptor protein TRIP6 antagonizes Fas-induced apoptosis but promotes its effect on cell migration. Mol Cell Biol 30:5582-5596.

Malleter, M., S. Tauzin, A. Bessede, R. Castellano, A. Goubard, F. Godey, J. Leveque, P. Jezequel, L. Campion, M. Campone, T. Ducret, G. Macgrogan, L. Debure, Y. Collette, P. Vacher, and P. Legembre. 2013. CD95L cell surface cleavage triggers a prometastatic signaling pathway in triple-negative breast cancer. Cancer Res 73:6711-6721.

Matsuno, H., K. Yudoh, Y. Watanabe, F. Nakazawa, H. Aono, and T. Kimura. 2001. Stromelysin-1 (MMP-3) in synovial fluid of patients with rheumatoid arthritis has potential to cleave membrane bound Fas ligand. J Rheumatol 28:22-28.

Motz, G. T., S. P. Santoro, L. P. Wang, T. Garrabrant, R. R. Lastra, I. S. Hagemann, P. Lal, M. D. Feldman, F. Benencia, and G. Coukos. 2014. Tumor endothelium FasL establishes a selective immune barrier promoting tolerance in tumors. Nat Med O'Reilly, L. A., L. Tai, L. Lee, E. A. Kruse, S. Grabow, W. D. Fairlie, N. M. Haynes, D. M. Tarlinton, J. G. Zhang, G. T. Belz, M. J. Smyth, P. Bouillet, L. Robb, and A. Strasser. 2009. Membrane-bound Fas ligand only is essential for Fas-induced apoptosis. Nature 461:659-663.

O'Reilly, K. E., F. Rojo, Q. B. She, D. Solit, G. B. Mills, D. Smith, H. Lane, F. Hofmann, D. J. Hicklin, D. L. Ludwig, J. Baselga, and N. Rosen. 2006. mTOR inhibition induces upstream receptor tyrosine kinase signaling and activates Akt. Cancer Res 66:1500-1508.

Orlinick, J. R., K. B. Elkon, and M. V. Chao. 1997. Separate domains of the human fas ligand dictate self-association and receptor binding. J Biol Chem 272:32221-32229.

Sato, T., S. Irie, S. Kitada, and J. C. Reed. 1995. FAP-1: a protein tyrosine phosphatase that associates with Fas. Science 268:411-415.

Schulte, M., K. Reiss, M. Lettau, T. Maretzky, A. Ludwig, D. Hartmann, B. de Strooper, O. Janssen, and P. Saftig. 2007. ADAM10 regulates FasL cell surface expression and modulates FasL-induced cytotoxicity and activation-induced cell death. Cell Death Differ 14:1040-1049.

Shin, M. S., N. Lee, and I. Kang. 2011. Effector T-cell subsets in systemic lupus erythematosus: update focusing on Th17 cells. Curr Opin Rheumatol 23:444-448.

Siegel, R. M., J. K. Frederiksen, D. A. Zacharias, F. K. Chan, M. Johnson, D. Lynch, R. Y. Tsien, and M. J. Lenardo. 2000. Fas preassociation required for apoptosis signaling and dominant inhibition by pathogenic mutations. Science 288:2354-2357.

Steinmetz, O. M., J. E. Turner, H. J. Paust, M. Lindner, A. Peters, K. Heiss, J. Velden, H. Hopfer, S. Fehr, T. Krieger, C. Meyer-Schwesinger, T. N. Meyer, U. Helmchen, H. W. Mittrucker, R. A. Stahl, and U. Panzer. 2009. CXCR3 mediates renal Th1 and Th17 immune response in murine lupus nephritis. J Immunol 183:4693-4704.

Suda, T., T. Takahashi, P. Golstein, and S. Nagata. 1993. Molecular cloning and expression of the Fas ligand, a novel member of the tumor necrosis factor family. Cell 75:1169-1178.

Tauzin, S., B. Chaigne-Delalande, E. Selva, N. Khadra, S. Daburon, C. Contin-Bordes, P. Blanco, J. Le Seyec, T. Ducret, L. Counillon, J. F. Moreau, P. Hofman, P. Vacher, and P. Legembre. 2011. The naturally processed CD95L elicits a c-yes/calcium/PI3K-driven cell migration pathway. PLoS Biol 9:e1001090.

Tuettenberg, J., M. Selz, K. M. Debatin, W. Hollburg, M. von Staden, M. Thiemann, B. Hareng, H. Fricke, and C. Kunz. 2012. Pharmacokinetics, pharmacodynamics, safety and tolerability of APG101, a CD95-Fc fusion protein, in healthy volunteers and two glioma patients. International immunopharmacology 13:93-100.

Vargo-Gogola, T., H. C. Crawford, B. Fingleton, and L. M. Matrisian. 2002. Identification of novel matrix metalloproteinase-7 (matrilysin) cleavage sites in murine and human Fas ligand. Arch Biochem Biophys 408:155-161.

Vives, E., P. Brodin, and B. Lebleu. 1997. A truncated HIV-1 Tat protein basic domain rapidly translocates through the plasma membrane and accumulates in the cell nucleus. J Biol Chem 272:16010-16017.

Wang, Y., S. Ito, Y. Chino, D. Goto, I. Matsumoto, H. Murata, A. Tsutsumi, T. Hayashi, K. Uchida, J. Usui, K. Yamagata, and T. Sumida. 2010. Laser microdissection-based analysis of cytokine balance in the kidneys of patients with lupus nephritis. Clin Exp Immunol 159:1-10.

Yang, J., Y. Chu, X. Yang, D. Gao, L. Zhu, X. Yang, L. Wan, and M. Li. 2009. Th17 and natural Treg cell population dynamics in systemic lupus erythematosus. Arthritis Rheum 60:1472-1483.

The invention claimed is:

1. A fusion protein, comprising a polypeptide having an amino acid sequence having at least 96, 97, 98, 99 or 100% identity with an amino acid sequence ranging from an amino-acid residue at position 175 to an amino-acid residue at position 191, 192, 193, 194, 195, 196, 197, 198, 199, 200, 201, 202, 203, 204, 205, 206, 207, 208, 209, or 210 as set forth in SEQ ID NO:1,
wherein said polypeptide is fused to a heterologous cell-penetrating peptide.

2. The fusion protein of claim 1, wherein said polypeptide has the amino acid identity of amino-acid residues 175 to 191 as set forth in SEQ ID NO: 1.

3. The fusion protein of claim 1, wherein said polypeptide has the amino acid identity of amino-acid residues 175 to 210 as set forth in SEQ ID NO: 1.

4. The fusion protein of claim 3, having said amino-acid residues 175 to 210 fused to said heterologous cell-penetrating peptide, wherein said heterologous cell-penetrating peptide is TAT, having a sequence identity as set forth in SEQ ID NO: 3 or SEQ ID NO:4.

5. The fusion protein of claim 1, wherein said heterologous cell-penetrating peptide is selected from the group consisting of: penetratin; TAT mitochondrial penetrating sequence; an internalization sequence derived from Drosophila Antennapedia/Penetratin (Antp) protein, having a sequence identity as set forth in SEQ ID NO: 2; and Transactivator of Transcription (TAT), having a sequence identity as set forth in SEQ ID NO:3 or SEQ ID NO: 4.

6. The fusion protein of claim 1, wherein said cell-penetrating peptide is TAT, having a sequence identity as set forth in SEQ ID NO: 3 or SEQ ID NO: 4.

7. A fusion protein comprising a polypeptide having an amino acid sequence having at least 96, 97, 98, 99 or 100% identity with an amino acid sequence ranging from an amino-acid residue at position 175 to an amino-acid residue at position 191, 192, 193, 194, 195, 196, 197, 198, 199, 200, 201, 202, 203, 204, 205, 206, 207, 208, 209, or 210 as set forth in SEQ ID NO:1 fused directly or via a spacer to at least one heterologous polypeptide.

8. The fusion protein of claim 7 wherein the at least one heterologous polypeptide is a cell-penetrating peptide, a Transactivator of Transcription (TAT) cell penetrating sequence, a cell permeable peptide or a membranous penetrating sequence.

9. The fusion protein of claim 8, wherein said heterologous peptide is TAT, having a sequence identity as set forth in SEQ ID NO: 3 or SEQ ID NO: 4.

10. A TAT-CID fusion protein, having a sequence identity as set forth in SEQ ID NO: 6.

11. A method for producing a fusion protein comprising
a polypeptide having an amino acid sequence ranging from an amino-acid residue at position 175 to an amino-acid residue at position 191, 192, 193, 194, 195, 196, 197, 198, 199, 200, 201, 202, 203, 204, 205, 206, 207, 208, 209, 210 as set forth in SEQ ID NO:1, and
a cell-penetrating peptide,
the method comprising the steps of:
(i) culturing a transformed host cell comprising a nucleic acid sequence encoding the fusion protein comprising the polypeptide and the cell-penetrating peptide, or a vector comprising an expression cassette comprising the nucleic acid sequence, under conditions suitable to allow expression of said fusion protein; and
(ii) recovering the expressed fusion protein.

* * * * *

SEQUENCE LISTING

<160> NUMBER OF SEQ ID NOS: 6

<210> SEQ ID NO 1
<211> LENGTH: 319
<212> TYPE: PRT
<213> ORGANISM: Homo sapiens

<400> SEQUENCE: 1

Arg Leu Ser Ser Lys Ser Val Asn Ala Gln Val Thr Asp Ile Asn Ser
1               5                   10                  15

Lys Gly Leu Glu Leu Arg Lys Thr Val Thr Val Glu Thr Gln Asn
            20                  25                  30

Leu Glu Gly Leu His His Asp Gly Gln Phe Cys His Lys Pro Cys Pro
            35                  40                  45

Pro Gly Glu Arg Lys Ala Arg Asp Cys Thr Val Asn Gly Asp Glu Pro
        50                  55                  60

Asp Cys Val Pro Cys Gln Glu Gly Lys Glu Tyr Thr Asp Lys Ala His
65                  70                  75                  80

Phe Ser Ser Lys Cys Arg Arg Cys Arg Leu Cys Asp Glu Gly His Gly
                85                  90                  95

Leu Glu Val Glu Ile Asn Cys Thr Arg Thr Gln Asn Thr Lys Cys Arg
            100                 105                 110

Cys Lys Pro Asn Phe Phe Cys Asn Ser Thr Val Cys Glu His Cys Asp
            115                 120                 125

Pro Cys Thr Lys Cys Glu His Gly Ile Ile Lys Glu Cys Thr Leu Thr
        130                 135                 140

Ser Asn Thr Lys Cys Lys Glu Glu Gly Ser Arg Ser Asn Leu Gly Trp
145                 150                 155                 160

Leu Cys Leu Leu Leu Leu Pro Ile Pro Leu Ile Val Trp Val Lys Arg
                165                 170                 175

Lys Glu Val Gln Lys Thr Cys Arg Lys His Arg Lys Glu Asn Gln Gly
            180                 185                 190

Ser His Glu Ser Pro Thr Leu Asn Pro Glu Thr Val Ala Ile Asn Leu
        195                 200                 205

Ser Asp Val Asp Leu Ser Lys Tyr Ile Thr Thr Ile Ala Gly Val Met
210                 215                 220

Thr Leu Ser Gln Val Lys Gly Phe Val Arg Lys Asn Gly Val Asn Glu
225                 230                 235                 240

Ala Lys Ile Asp Glu Ile Lys Asn Asp Asn Val Gln Asp Thr Ala Glu
                245                 250                 255

Gln Lys Val Gln Leu Leu Arg Asn Trp His Gln Leu His Gly Lys Lys
            260                 265                 270

Glu Ala Tyr Asp Thr Leu Ile Lys Asp Leu Lys Lys Ala Asn Leu Cys
        275                 280                 285

Thr Leu Ala Glu Lys Ile Gln Thr Ile Ile Leu Lys Asp Ile Thr Ser
            290                 295                 300

Asp Ser Glu Asn Ser Asn Phe Arg Asn Glu Ile Gln Ser Leu Val
305                 310                 315

<210> SEQ ID NO 2
<211> LENGTH: 16
<212> TYPE: PRT
<213> ORGANISM: Artificial
<220> FEATURE:
<223> OTHER INFORMATION: Penetratin

<400> SEQUENCE: 2

```
Arg Gln Ile Lys Ile Trp Phe Gln Asn Arg Arg Met Lys Trp Lys Lys
1               5                   10                  15

<210> SEQ ID NO 3
<211> LENGTH: 11
<212> TYPE: PRT
<213> ORGANISM: Artificial
<220> FEATURE:
<223> OTHER INFORMATION: TAT

<400> SEQUENCE: 3

Tyr Gly Arg Lys Lys Arg Arg Gln Arg Arg Arg
1               5                   10

<210> SEQ ID NO 4
<211> LENGTH: 9
<212> TYPE: PRT
<213> ORGANISM: Artificial
<220> FEATURE:
<223> OTHER INFORMATION: TAT DOMAIN

<400> SEQUENCE: 4

Arg Lys Lys Arg Arg Gln Arg Arg Arg
1               5

<210> SEQ ID NO 5
<211> LENGTH: 21
<212> TYPE: PRT
<213> ORGANISM: Artificial
<220> FEATURE:
<223> OTHER INFORMATION: TAT-CONTROL

<400> SEQUENCE: 5

Arg Lys Lys Arg Arg Gln Arg Arg Arg Gly Gly Ser Ile Glu Leu Asp
1               5                   10                  15

Asp Pro Arg Pro Arg
            20

<210> SEQ ID NO 6
<211> LENGTH: 45
<212> TYPE: PRT
<213> ORGANISM: Artificial
<220> FEATURE:
<223> OTHER INFORMATION: TAT-CID

<400> SEQUENCE: 6

Arg Lys Lys Arg Arg Gln Arg Arg Lys Arg Lys Glu Val Gln Lys
1               5                   10                  15

Thr Cys Arg Lys His Arg Lys Glu Asn Gln Gly Ser His Glu Ser Pro
            20                  25                  30

Thr Leu Asn Pro Glu Thr Val Ala Ile Asn Leu Ser Asp
            35                  40                  45
```